United States Patent [19]
Maras et al.

[11] Patent Number: 5,834,251
[45] Date of Patent: Nov. 10, 1998

[54] METHODS OF MODIFYING CARBOHYDRATE MOIETIES

[75] Inventors: Marleen Maras, Gentbrugge; Roland Contreras, Merelbeke, both of Belgium

[73] Assignee: Alko Group Ltd., Helsinki, Finland

[21] Appl. No.: 366,800

[22] Filed: Dec. 30, 1994

[51] Int. Cl.$^6$ ............................. C12P 21/00; C12P 19/18; C12P 1/02
[52] U.S. Cl. .............................. 435/71.1; 435/72; 435/85; 435/97; 435/99; 435/69.1; 435/171; 435/68.1
[58] Field of Search ............................... 435/71.1, 85, 97, 435/99, 171, 72, 69.1, 68.1

[56] References Cited

U.S. PATENT DOCUMENTS

| | | | |
|---|---|---|---|
| 4,770,994 | 9/1988 | Rittenhouse | 435/7 |
| 5,180,674 | 1/1993 | Roth | 435/288 |
| 5,272,066 | 12/1993 | Bergh et al. | 435/97 |
| 5,324,663 | 6/1994 | Lowe | 435/320.1 |

FOREIGN PATENT DOCUMENTS 0 244 234   11/1987   European Pat. Off. .

OTHER PUBLICATIONS

Burke, J. et al., "The Transmembrane and Flanking Sequences of β1,2–N–Acetylglucosaminytransferase I Specify medial–Golgi Localization," *J. Biol. Chem.* 267(34):24433–24440 (1992).

Carrez, D. et al., "Heterologous gene expression by filamentous fungi: secretion of human interleukin–6 by *Aspergillus nidulans*," *Gene* 94:147–154 (1990).

Chiba, Y. et al., "The Carbohydrate Moiety of the Acid Carboxypeptidase from *Aspergillus saitoi*," *Curr. Microbial.* 27:281–288 (1993).

Contreras R. et al., "Efficient Kex2–like Processing of a Glucoamyase–Interleukin–6 Fusion Protein by *Aspergillus nidulans* and Secretion of Mature Interleukin–6," *Bio/Technology* 9:378–381 (1991).

Dwek, R.A. et al., "Analysis of Glycoprotein–Associated Oligosaccharides," *Annu. Rev. Biochem.* 62:65–100 (1993).

Harkki, A. et al., "A Novel Fungal Expression System: Secretion of Active Calf Chymosin from the Filamentous Fungus *Trichoderma reesei*," *Bio/Technology* 7:596–601 (1989).

Keskar, S.S. et al., "Production and Properties of α–Mannosidase from *Aspergillus sp.*," *Biotech. Lett.* 15(7):685–690 (1993).

Kukuruzinska, M.A. et al., "Protein Glycosylation in Yeast," *Ann. Rev. Biochem.* 56:915–944 (1987).

Nevalainen, H., "Genetic Improvement of Enzyme Production in Industrially Important Fungal Strains," *Presented at the Univ. of Helsinki on Nov. 29, 1985*.

Salovuori, I. et al., "Low Molecular Weight High–Mannose Type Glycans in a Secreted Protein of the Filamentous Fungus *Trichoderma reesei*," *Bio/Technology* 5:152–156 (1987).

Schachter, Hl., "The 'yellow brick road' to branched complex N–glycans," *Glycobiology* 1(5):453–461 (1991).

Shoemaker, S. et al., "Characterization and Properties of Cellulases Purified From *Trichoderma reesei* Strain L27," *Bio/Technology* 1:687–690 (1983).

Stanley, P., "Chinese Hamster Ovary Cell Mutants with Multiple Glycosylation Defects for Production of Glycoproteins with Minimal Carbohydrate Heterogeneity," *Molec. Cell. Biol.* 9(2):377–383 (1989).

Stanley, P., "Glycosylation engineering ," *Glycobiology* 2(2):99–107 (1992).

Uusitalo, J.M. et al., "Enzyme production by recombinant *Trichoderma reesei* strains," *J. Biotech.* 17:35–50 (1991).

van den Hondel, C. et al., "Heterologous Gene Expression in Filamentous Fungi," in: More Gene Manipulations in Fungi, Bennett et al., eds., pp. 396–428 (1991).

Van Brunt, J., "Fungi: The Perfect Hosts?" *Bio/Technology* 4:1057–1059 and 1060–1062 (1986).

Varki, A., "Biological roles of oligosaccharides: all of the theories are correct," *Glycobiology* 3(2):97–130 (1993).

Toone et al, Tetrahedron 45(17): 5365–5422 (1989).

*Primary Examiner*—John W. Rollins
*Assistant Examiner*—Francisco C. Prats
*Attorney, Agent, or Firm*—Sterne,Kessler, Goldstein & Fox, p.l.l.c.

[57] ABSTRACT

The invention is directed to methods of converting high mannose type glycosylation patterns to hybrid or complex type glycosylation patterns.

20 Claims, 16 Drawing Sheets

METHODS OF MODIFYING CARBOHYDRATE MOIETIES

FIELD OF THE INVENTION

The invention is directed to a method for converting glycosylation patterns on proteins and cells to a hybrid or complex pattern. This is especially useful for recombinantly-produced, therapeutic proteins that are to be administered to a mammalian, especially human, patient.

BACKGROUND OF THE INVENTION

Glycosylation affects many properties of a glycoprotein, including proper protein folding, protease resistance/sensitivity, intracellular trafficking and compartmentalization, secretion, inter- and intra-molecular associations, intermolecular affinities, tissue targeting and biological half-life. Glycosylation patterns may also significantly alter the biological activity, solubility, clearance, intermolecular aggregation and antigenicity, especially of those proteins that are administered therapeutically in vivo.

Unfortunately, the recombinant production of many proteins can greatly alter their glycosylation pattern. Proteins expressed in bacteria are completely unglycosylated. Baker's yeast glycosylation patterns are not equivalent to mammalian counterparts and are highly antigenic in mammals (Ballou, C. E., 1982. In Strathern, J. N. et al. (eds). *The Molecular Biology of the Yeast Saccharomyces. Metabolism and Gene Expression*. Cold Spring Harbor Laboratory Press, New York, pp. 335–360).

Similarly, non-complex glycosyl moieties are observed when insect cells, such as the popular Sf9 baculovirus expression system, are used to express mammalian proteins (Davidson et al., *Biochemistry*, 29:2828–2838 (1990); Bahl, O .P. et al., in *Cell Surface and Extracellular Glycoconjugates—Structure and Function*, D. D. Roberts et al., eds., Academic Press, Inc. 1993 pp. 245–270). High mannose (Man) and hybrid oligosaccharides are synthesized on proteins produced in insect cells. The primary structures of these glycans are not different from those found on certain mammalian proteins such as ribonuclease B, thyroglobin, tissue plasminogen activator (the latter one has a mixed population of high mannose and complex structures at its glycosylation sites).

Small mammalian cells cultures are practical for use in laboratory mammalian gene expression experiments. However, the cost and difficulties of expressing large quantities of therapeutic recombinant glycoproteins in mammalian cell cultures are prohibitive. Therefore, there is a need for a host that is capable of producing large quantities of recombinant proteins that possess, or can be modified to possess, a glycosylation pattern that is similar to that produced by mammalian cells.

Filamentous fungi, for example, Trichoderma, have certain advantages as recombinant hosts. It is easy to grow large amounts of these fungi and they have the ability to glycosylate and efficiently secrete large yields of recombinant mammalian proteins into the medium, making isolation relatively easy. In addition, the glycosylation pattern on such proteins is more similar to humans than that of baker's yeast. However, there are still differences, which places wild-type fungal glycosylation patterns at a structural and functional disadvantage when in vivo efficacy of a protein requires a specific type of glycosylation. For example, terminal sialic acid residues are important to the functioning of a protein in a mammalian system, as they impede glycoprotein clearance from the mammalian bloodstream. The mechanism behind the increased biologic half-life of sialylated molecules is believed to lie in their decreased recognition by lectins (Drickamer, K., *J. Biol. Chem.* 263:9557–9560 (1988)). However, fungal cells are not capable of adding such units. Glycoproteins synthesized in fungal cells are asialic.

Another disadvantage presented by the inability to generate complex glycoprotein moieties lies in the presence of terminal mannose residues. Glycoproteins terminating in mannose residues are ligands for mannose-binding proteins on macrophages and cells from the reticulo-endothelial system (Ezekowitz et al., *J. Cell Sci. Suppl.* 9:121–133 (1988)). While this can be useful in some limited instances, as for targeting purposes, this has an undesirable pharmacological consequence for most recombinant proteins—e.g., the rapid clearance of the compound from the blood. Rapid clearance may deleteriously effect the administered agent's pharmacokinetics and decrease its therapeutic potential or increase its toxicity. Thus, recombinantly produced non-complex glycosylation patterns hamper the use of recombinantly made glycoproteins for human therapeutic use (Sareneva, T. et al., *Interferon Res.* 13:267–269 (1993)).

These disadvantages may block the biological or pharmacologic usefulness of mammalian proteins generated using fungal transformation systems. Therefore, there has been a long-felt need in the glycoprotein industry to devise an (in vitro) glycosylation system that would provide complex type glycosylation patterns similar to those found on proteins from the higher eukaryotes.

SUMMARY OF THE INVENTION

Recognizing the need for the large scale, economical production of recombinant proteins that have a mammalian glycosylation pattern, the inventors have investigated glycosyl residue processing in mammalian and fungal cells. These studies have led to the discovery that filamentous fungi such as Trichoderma are capable of secreting a desired protein in an immature glycosylated precursor form that is amenable to in vitro processing to a hybrid type mammalian glycosylation pattern. This discovery has resulted in the development of methods of preparing hybrid and complex protein glycosylation patterns, similar to those found in mammalian hosts.

Accordingly, in a first embodiment, the glycosylation pattern of a desired glycosylated protein (glycoprotein) is sequentially modified by reaction with N-acetylglucosaminyl-transferase I (GlcNAc Tr I), galactosyltransferase and sialyltransferase, so as to produce a protein having a hybrid-type glycosylation pattern with terminal sialic acid(s) similar to that of mammalian cells.

Accordingly, in a further embodiment, the glycosylation pattern of a desired glycosylated protein is sequentially modified first by reacting such protein with mannosidase, and then by reaction with GlcNAc Tr I, galactosyltransferase and sialyltransferase, so as to produce a hybrid type glycosylation pattern with at least one terminal sialic acid residue similar to that of mammalian cells.

Accordingly, in a further embodiment, glycosylated proteins are expressed in, and preferably secreted from, a fungal host that has been transformed with GlcNAc Tr I, and modified by sequential reaction with galactosyltransferase and sialyltransferase so as to produce a hybrid-type glycosylation pattern with terminal sialic acid, a structure similar to that of mammalian cells.

Accordingly, in a further embodiment, the glycosylation pattern of the desired glycosylated protein produced in a fungal host, preferably Trichoderma, that has been transformed with GlcNAc Tr I, is modified by reacting such protein sequentially with galactosyltransferase and sialyltransferase, so as to produce a protein having a hybrid-type glycosylation pattern with a terminal sialic acid structure similar to that of mammalian cells.

Accordingly, in a further embodiment, the immature glycosylated form of a desired glycosylated protein is produced in a fungal host, preferably Trichoderma, that has been transformed with a recombinant gene encoding GlcNAc Tr I, preferably human GlcNAc Tr I, and is modified by in vitro reaction with mannosidase, so as to produce a protein having a mono-antennary complex glycosylation pattern in one in vitro step.

Accordingly, in a further embodiment, any of the above proteins having a hybrid type glycosylation pattern are converted to a complex pattern by reactions with an $\alpha$ 1,2-; $\alpha$ 1,3-; and/or $\alpha$ 1,6- mannosidase.

BRIEF DESCRIPTION OF THE DRAWINGS

FIG. 1 is a diagram that illustrates the conversion of high mannose oligosaccharides (glycosyl structures) to hybrid oligosaccharides after the reaction of high mannose structures with $\alpha$-1,2 mannosidase, GlcNAc Tr I, $\beta$-1,4 galactosyl transferase (shown as GalTr), and $\alpha$-2,6 sialyltransferase (shown as NeuNAc T). The conversion of fungal glycoprotein high mannose oligosaccharides (glycosyl structures) to hybrid structures occurs as a result of this illustrated series of reactions.

FIG. 1A is a diagram that illustrates the conversion of hybrid oligosaccharides (glycosyl structures) to complex type oligosaccharides after the reaction of hybrid structures with an aspecific (non-specific) $\alpha$-mannosidase.

FIG. 2 shows a map of plasmid pCAGGS. The major divisions are lengths of 1000 bp, the subdivisions are lengths of 200 bases. The length is approximately 4811 bp. AG:$\beta$-actin/$\beta$-globin hybrid promoter; SVORI:bidirectional origin of SV40; RBS: lac operon ribosome binding site; polyA: polyA signal of the SV40 early region (clockwise arrow) or late region (counterclockwise arrow); Ori: Eco-pMBI origin or plasmid replication; AMP: ampillicin resistance gene; CMV: CMV-IE enhancer; lac: lac promoter; rGBf (plasmid bases 10–182): partial exon 3 and 3' untranslated region and poly A site of the rabbit $\beta$-globin gene; 3FR (plasmid bases 183–541): 3'-flanking region of rabbit $\beta$-globin gene.

FIG. 3 shows a map of plasmid pSCGAL1MF3. The major divisions are lengths of 500 bp, the subdivisions are lengths of 100 bases. The length is approximately 3477 bp. AMP: ampicillin resistance gene; ORI: origin of plasmid replication (Eco-pMB1); lac: lac promoter; RBS: lac operon ribosome binding site; GAL1: Gal1 promoter, PREMF: $\alpha$-mating factor 1 prepro sequence; lacZ: LacZ$\alpha$ gene.

FIG. 4 shows a map of plasmid pCAMFhGNTIf$_1$, containing a human gene fragment encoding N-acetylglucosaminyltransferase I (hGlcNAc-Tr I). The major divisions are lengths of 1000 bp, the subdivisions are lengths of 200 bases. The length is approximately 6223 bp. AMP: ampicillin resistance gene; ORI: origin of plasmid replication (Eco-pMB1); lac: lac promoter; RBS: lac operon ribosome binding site; PREMF: $\alpha$-mating factor 1 prepro sequence; rGBf (plasmid bases 1–170): partial exon 3 and 3' untranslated region and poly A site of the rabbit $\beta$-globin gene; 3FR (plasmid bases 171–530): 3'-flanking region of rabbit $\beta$-globin gene; SVORI: bidirectional origin of replication of SV40; poly A: poly A signal of the SV40 early (clockwise arrow) or late region (counterclockwise arrow); CMV: CMV-IE enhancer; Ac: chicken $\beta$-actin promoter.

FIG. 4A diagrams the insertion of the hGNTI fragment into pUC18; FIG. 4B diagrams the extraction of the GAL1-PREMF fragment from pSCGAL1MF3 and its insertion into pUC18; FIG. 4C diagrams the construction of the pUC18 plasmid that contains the hGNTI sequence (without its signal sequence) after the PREMF signal sequence; and FIGS. 4D and 4E diagram the final construction of pCAMFhGNTIf1 by inserting the PREMF-hGNTI fragment that had been taken from the vector constructed in FIG. 4C into pCAGGS.

FIG. 5 shows an autoradiogram that was obtained after exposure of an X-ray film to radiolabelled glycoproteins that had been separated on an SDS-polyacrylamide gel electrophoresis (SDS-PAGE). The following GlcNAc Tr I substrates were added as noted: Lane 1, no substrate protein added; lane 2, human transferrin added as a negative control; lane 3, S. cerevisiae invertase added as a negative control; lane 4, ovalbumin added as a positive control; lane 5, cellulases from Trichodenna; lane 6, proteins secreted from T. reesei mutant RUTC 30.

FIG. 6 shows an autoradiogram that was obtained after exposure of an X-ray film to radiolabelled oligosaccharide structures that had been separated on a thin layer chromatography plate (TLC). The following were added to the reaction mixture containing GlcNAc Tr I: Lane 1, no oligosaccharides added to reaction; lanes 2 and 3, high mannose oligosaccharides from ribonuclease B hydrazinolysis, Oxford Glycosystems, (lane 2), and, Man$_5$Gn from mannosidosis urine, Sanbio, (lane 3), were reacted as positive controls; lane 4, oligosaccharides isolated from Trichoderma cellulases; lane 5, oligosaccharides isolated from secreted proteins from T. reesei mutant RUTC 30; lane 6, glycosyl structures released from S. cerevisiae invertase as negative control.

FIG. 7 shows an autoradiogram that was obtained after exposure of an X-ray film to radiolabelled glycoproteins that had been separated on 12.5% SDS-PAGE. Lane 1, the incorporation of radioactive 2-deoxy-2-N-acetylamino-D-glucose (GlcNAc) on CBH I is shown; lane 2, a clear electrophoretic shift of CBH I was the consequence of the incorporation of radioactive sialic acid is shown.

FIG. 8 shows the electrophoretic resolution of ANTS-oligosaccharides prepared from T. reesei RUTC 30 glycoproteins. Lane 1: the CBH I digest; lane 2: CBH I oligosaccharides treated with A. saitoi $\alpha$-1,2-mannosidase; lane 3: digest from a mixture of T. reesei RUTC 30 secreted proteins; lane 4: analogous to lane 3, but with $\alpha$-1,2-mannosidase treatment; lane 5: bovine ribonuclease B digest; M: molecular weight markers (a:maltotetraose; b:maltopentaose; c:maltohexaose; d:maltoheptaose; e:maltooctaose; f:maltononaose).

FIG. 9 shows an autoradiogram of a thin layer chromatogram as above, separating free oligosaccharides pretreated with $\alpha$-1,2 mannosidase and subsequently treated with GlcNAc Tr I and UDP-($^{14}$C)GlcNAc (uridinediphospho-2-deoxy-2-N-acetylamino-D-$^{14}$C-glucose). To the GlcNAc Tr I reaction mixtures, the following were added: Lane 1, oligosaccharides were not added; lane 2, Man$_5$GlcNAc (Sanbio), an acceptor substrate for GlcNAc Tr I, was added as a positive control; lanes 3 and 4, respectively, S. cerevisiae invertase oligosaccharides not pretreated and pretreated with $\alpha$-1,2 mannosidase; lanes 5 and 6, respectively, oligosaccharides from Trichodenna cellulases (Fluka, Buchs, Switzerland) not pretreated and pretreated with α-1,2 mannosidase; lanes 7 and 8, respectively, oligosaccharides from *T. reesei* mutant RUTC 30 not pretreated and pretreated with α-1,2 mannosidase.

FIG. 10 shows an autoradiogram of an SDS-PAGE separating glycoproteins reacted with GlcNAc Tr I and UDP-($^{14}$C)GlcNAc, with or without "pretreatment" with *A. Saito* α-1,2 mannosidase. Lanes 1 and 2, respectively, no protein acceptor substrate without and with α-1,2 mannosidase treatment; lanes 3 and 4, respectively, transferrin without and with pretreatment with α-1,2 mannosidase; lanes 5 and 6, respectively, *S. cerevisiae* invertase without and with pretreatment with α-1,2 mannosidase; lanes 7 and 8, respectively, ovalbumin without and with pretreatment with α-1,2 mannosidase; lanes 9 and 10, respectively, Trichoderma cellulases (Fluka, Buchs, Switzerland) without and with pretreatment with α-1,2 mannosidase.

DETAILED DESCRIPTION OF THE PREFERRED EMBODIMENTS

Figure 1:
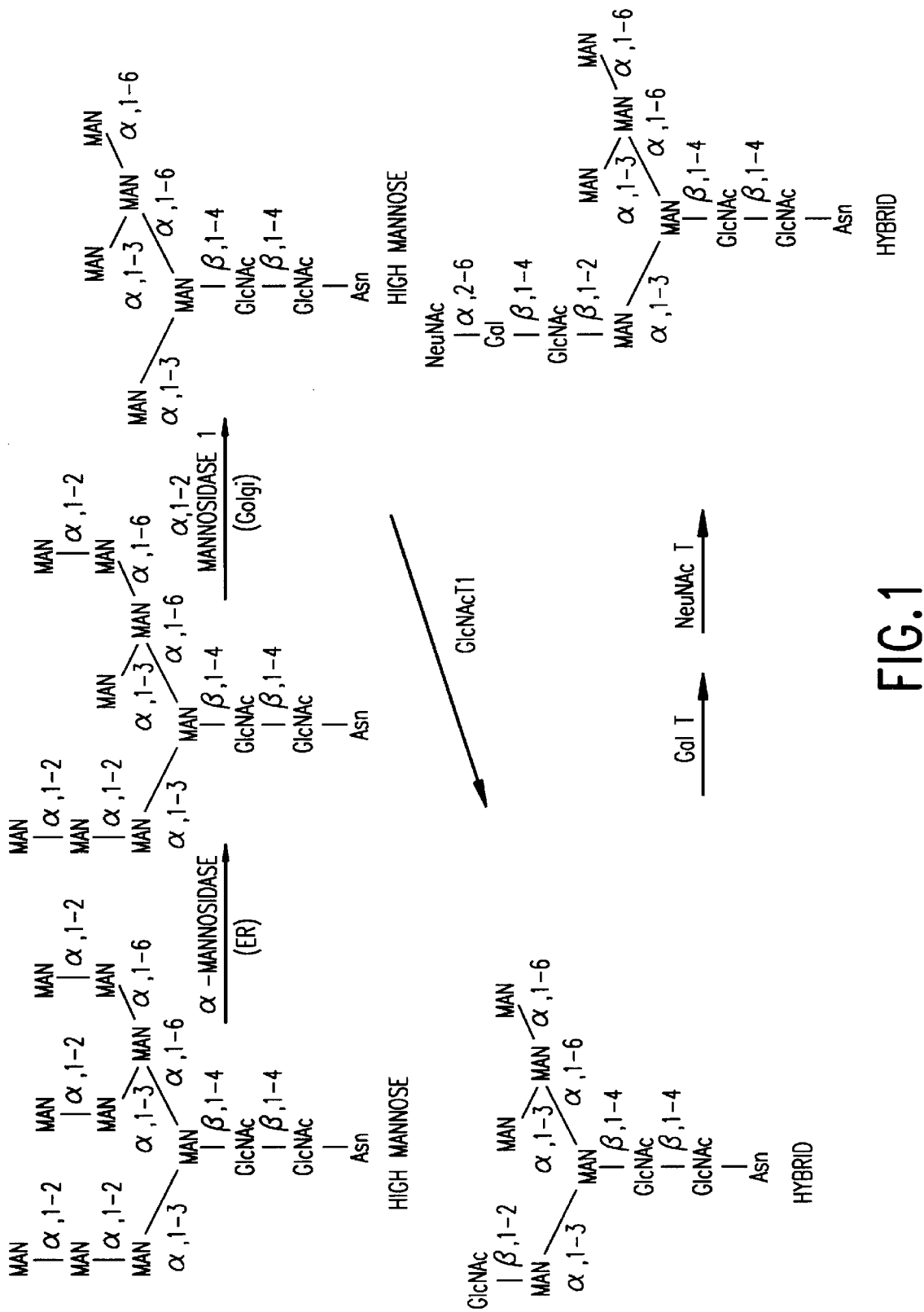
FIG. 1.
Figure 1A:
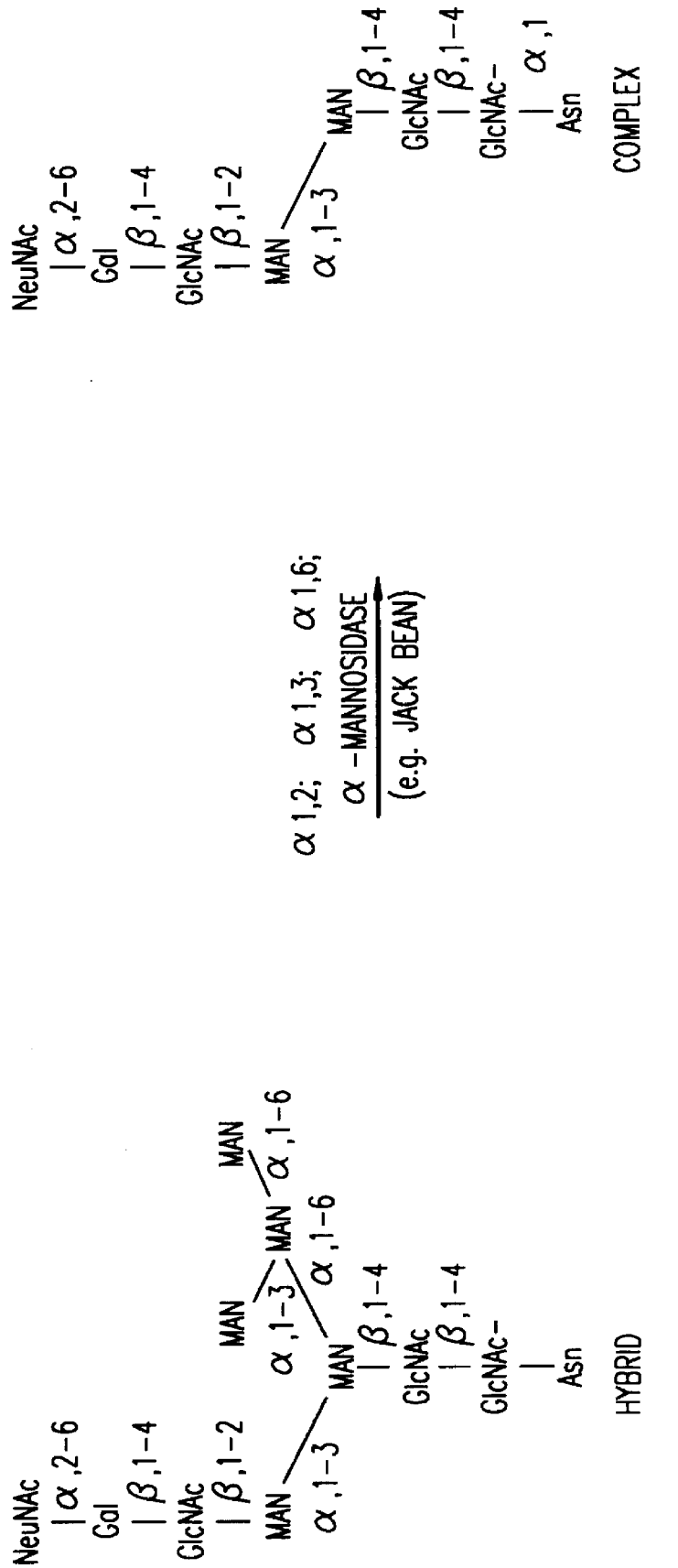
FIG. 1A.

In the following description, reference will be made to various methodologies known to those skilled in the art of molecular genetics, microbiology and general biology. Publications and other materials setting forth such known methodologies to which reference is made are incorporated herein by reference in their entireties as though set forth in full.

General principles of glycoprotein biology and of glycoprotein structural analysis are set forth, for example, in *Glycoprotein Analysis in Bio medicine*, edited by E. F. Hounsell, Humana Press, Totowa, N.J. (1993), and in *Cell Surface and Extracellular Glycoproteins, Structure and Function*, edited by D. D. Roberts and R. P. Mecham, Academic Press, Inc., San Diego, Calif. (1993).

General principles of the bi ochemistry and molecular biology of the filamentous fungi and Trichoderma are set forth, for example, in Finkelstein, D. B. et al., eds., *Biotechnology of Filamentous Fungi: Technology and Products*, Butterworth-Heinemann, publishers, Stoneham, Mass. (1992), and Bennett, J. W. et al., *More Gene Manipulations in Fungi*, Academic Press—Harcourt Brace Jovanovich, publishers, San Diego, Calif. (1991).

I. Definitions

Unless defined otherwise, all technical and scientific terms used herein have the same meaning as is commonly understood by one of skill in the art to which this invention belongs. In the description that follows, a number of terms used in glycoprotein technology are extensively utilized. In order to provide a clear and consistent understanding of the specification and claims, including the scope to be given such terms, the following definitions are provided.

"Glycosylation pattern" refers to a characteristic structure, number or location of oligosaccharide structures associated with a macromolecule, such as a protein, or typical of a specific cell type or species.

"Wild-type glycosylation pattern" refers to the characteristic native structure, number or location of oligosaccharide structures that are associated with a macromolecule, such as a protein, or found on a specific cell type or species.

"O-linked" oligosaccharides are those oligosaccharides that are linked to a peptide backbone through threonine or serine.

"N-linked" oligosaccharides are those oligosaccharides that are linked to a peptide backbone through asparagine, by way of an asparagine-N-acetylglucosamine linkage. The N-linked oligosaccharides are also called "N-glycans." All N-linked oligosaccharides have a common pentasaccharide core of Man$_3$GlcNAc$_2$ (Mannose$_3$GlucoseNAcetyl$_2$) (Glucose can be abbreviated as Glc and Gluc). They differ in the presence of, and in the number of branches (also called antennae) of peripheral sugars such as fucose and sialic acid.

N-linked oligosaccharides are categorized according to their branched constituents. If the branched constituent is only mannose, the oligosaccharide is said to be a "high mannose N-glycan." As used herein "high mannose" or "high-mannose type" oligosaccharide or glycosyl structure means an oligosaccharide with additional α-mannose residues linked to the outer core structure Man$_3$GlcNAc$_2$, and no fucose or sialic acid residues at the free ends of the oligosaccharide branches.

A "complex" or "complex-type" oligosaccharide or glycosyl structure means the structure of an oligosaccharide with typically two to six outer branches with a sialyllactosamine sequence linked to an outer core structure Man$_3$GlcNAc$_2$. A complex N-glycan has at least one branch, and preferably at least two, of alternating GlcNAc and galactose (Gal) residues that terminate in oligosaccharides such as, for example: NeuNAc-; NeuAcα2-6GalNAcα1-; NeuAcα2-3Galβ1-3GalNAcα1-; NeuAcα2-3/6Galβ1-4GlcNAcβ1-; GlcNAcα1-4Galβ1-(mucins only); Fucα1-2Galβ1-(blood group H);

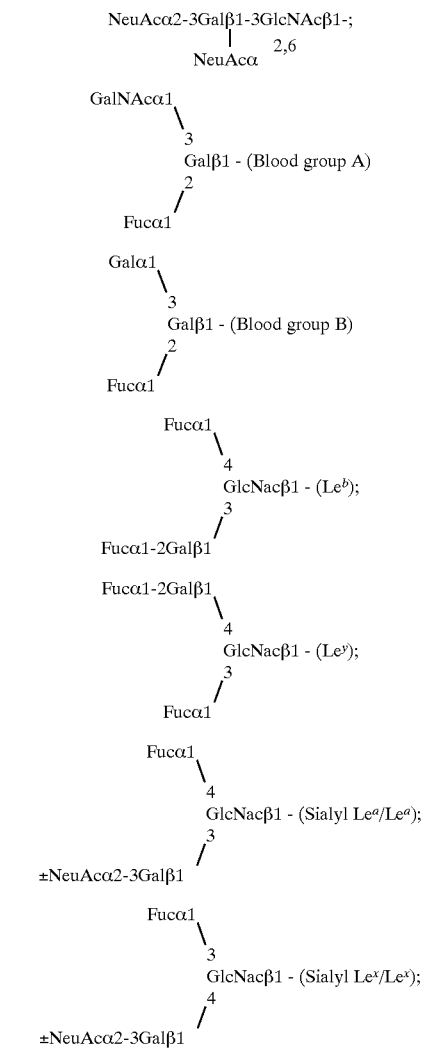

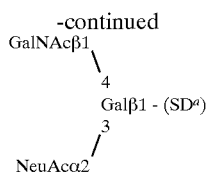

Sulfate esters can occur on galactose, GalNAc, and GlcNAc residues, and phosphate esters can occur on mannose residues. NeuAc (Neu: neuraminic acid; Ac:acetyl) can be O-acetylated or replaced by NeuGl (N-glycolylneuraminic acid). Complex N-glycans may also have intrachain substitutions of bisecting GlcNAc and core fucose (Fuc).

"Hybrid N-glycans" have only mannose residues on the Manα1-6 arm of the core and one or two complex antennae on the Manα1-3 arm.

An "acceptor substrate" is an oligosaccharide, the specific structure of which is recognized as a substrate by an enzyme, such that reaction with such enzyme adds certain sugar residues to said acceptor substrate. For example, the oligosaccharide $Man_5GlcNAc_2$ is an acceptor substrate for GlcNAc Tr I, the first glycosyltransferase involved in complex carbohydrate formation.

By an "immature precursor" glycosylation pattern, or N-glycan structure is meant a high mannose structure. According to the invention, "immature" structures can be "matured" to a hybrid or complex type structure by treatment with enzymes that add the appropriate units of the hybrid or complex-type oligosaccharides, with or without the removal of the mannose residues as necessary.

By "sequentially modified" is meant that an oligosaccharide (glycan) structure is enzymatically modified in an ordered manner, involving two or more enzymatic reaction such that at least one reaction precedes the other. This is also referred to as a "cascade" series of enzymatic reactions.

By "reacting a protein with an enzyme" is meant that the protein is provided in a reaction mixture that contains all the required components for catalyzing the enzyme's inherent activity to modify such protein.

Linkage between monosaccharides units in a glycan can be to any of the hydroxyl groups with either a β or an α anomeric configuration. When drawn as shown below (for example at carbon 1 ("1" below) of GlcNAc and sialic acid), the β or α configuration is depicted as a line above or below the plane of the monosaccharide ring, respectively.

The pyranose form of β-D-N-acetylglucosamine (GlcNAc) is:

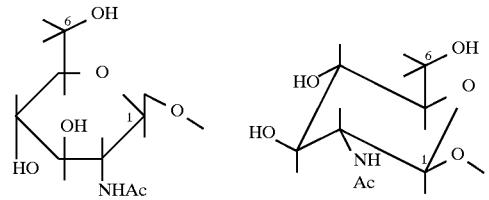

The structure of sialic acid is:

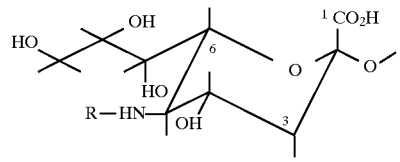

where $R=CH_3-CO$-(N-acetylneuraminic acid) or $CH_3OH-CO$-(N-glycolylneuraminic acid); the hydroxyl groups can be substituted with different acyl substituents and those at C8 and C9 with additional sialic acid residues.

Certain abbreviations are used herein as are common in the art, such as: "Ac" for acetyl; "glc" for glucose; "fuc" for fucose; "GlcNAc" for N-acetylglucosamine; "man" for mannose; "PNGase F" for peptide N-glycosidase F (EC 3.2.2.18).

As used herein, "GlcNAc Tr I" means N-acetylglucosaminyltransferase I.

II. The Glycosylation Pathway

In glycoproteins, potential N-glycosylation sites contain the sequence asparagine-X-serine (or threonine), where X can be any amino acid except proline. Proteins can be engineered to contain artificial N-glycosylation sites, or the natural site may be used.

The methods of the invention will be better understood by reference to the glycosylation pathway as described below. It is believed that the early events of N-glycan synthesis that are executed in the endoplasmic reticulum are identical in yeasts, plants and higher eukaryotes and fungi. The pathway of N-glycosylation of proteins in eukaryotic cells generally follows this pattern. First, a lipid-linked precursor oligosaccharide (I):

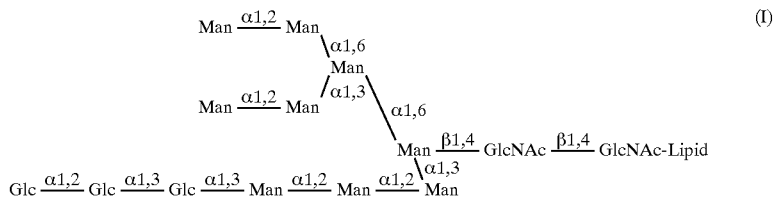

is transferred from the lipid and attached an Asn on the target protein through the action of an oligosaccharyltransferase to form (II):

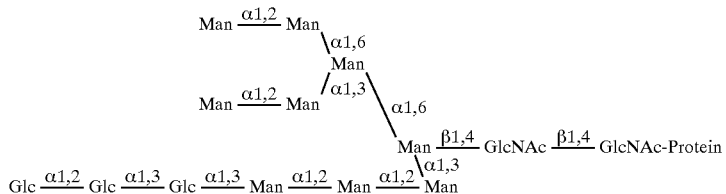

(II)

This is also abbreviated: Glc$_3$Man$_9$GlcNAc$_2$-protein. The enzyme α-1,2 glucosidase I then removes the terminal glucose residue, and α-1,3 glucosidase II removes the second and third glucose residues to leave (III):

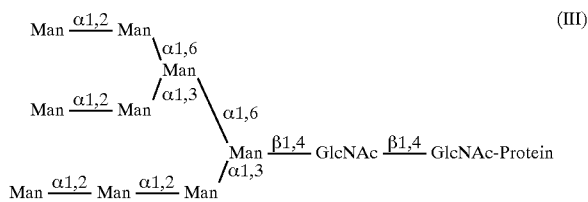

(III)

This is an example of a "high-mannose type" glycosylation. This is also abbreviated: Man$_9$GlcNAc$_2$-protein.

The final step in the rough endoplasmic reticulum is the removal of one mannose residue. Remaining steps are performed in endoplasmic reticulum (ER) and the Golgi apparatus. Up to this point, the glycosylation pathway of both yeast and mammalian cells is the same. However, steps in the cis-Golgi differ between yeast and the higher eukaryotes. Yeast add mannoses by the action of mannosyltransferases, the result of which is a high mannose type glycosylation in the glycosylated product. However, higher eukaryotes remove three additional mannoses, with α-mannosidase I; in some cases, this trimming also takes place in the ER. The result is the product (IV):

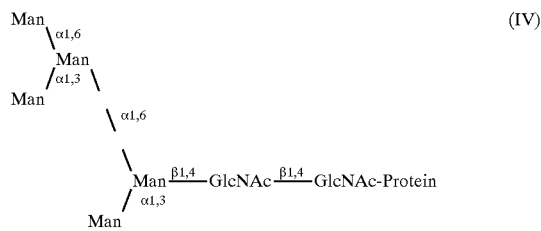

(IV)

This is also a "high mannose" structure and is abbreviated: Man$_5$GlcNAc$_2$-protein. The high energy sugar nucleotide, UDP-GlcNAc, serves as a substrate for GlcNAc Tr I to transfer a GlcNAc moiety to (IV) to produce (V):

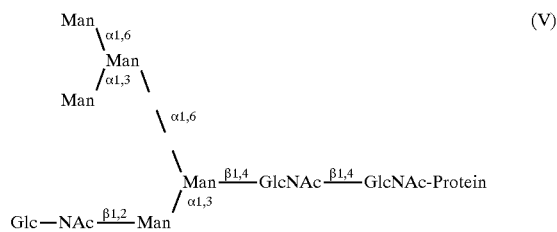

(V)

This is a hybrid-type structure and is abbreviated: GlcNacMan$_5$GlcNAc$_2$-protein. α-Mannosidase II recognizes this substrate and removes additional mannose residues to result in the "hybrid type" structure (VI):

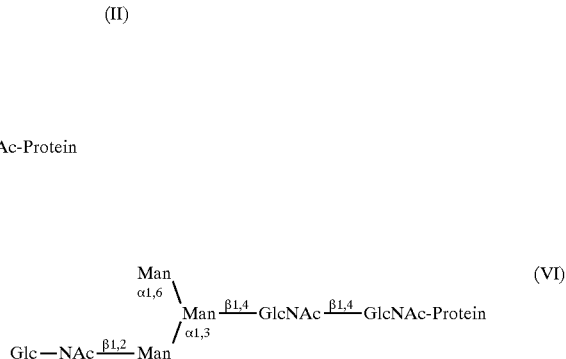

(VI)

This is abbreviated: GlcNacMan$_3$GlcNAc$_2$-protein. This can serve as a substrate for any of UDP-GlcNAc, UDP-Gal or CMP-sialic acid (SA), and GlcNAc-transferase II, galactosyltransferse or sialyltransferase, respectfully, to yield a "complex type" glycoslyation pattern, for example, as shown below (VII):

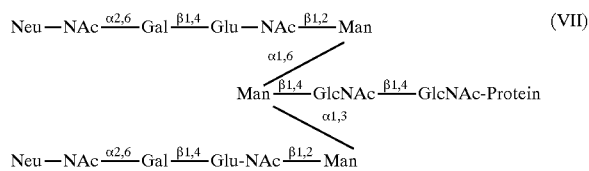

(VII)

III. Glycosylation Modification Enzymes

The glycosylation modification enzymes that are useful in the methods of the invention include transferases and mannosidases. Mannose residues that are linked by an α1,2 linkage are those mannose residues that can be removed in vivo or in vitro by a "specific" α1,2 mannosidase, such as that of *Aspergillus saitoi*. GlcNAc Tr I is very specific and only transfers GlcNAc to the less periferic α1,3-linked mannose of a Man5GlcNAc2 structure (an appropriate substrate is shown as structure IV, above). After transfer of GlcNAc, galactose and sialic acid to Man5GlcNAc2, the remaining α1,3 and α1,6-linked mannose residues can be removed in vivo or in vitro using an "aspecific" mannosidase such as, for example, the commercially available Jack bean mannosidase, thus converting a hybrid structure to a complex one.

Transferases such as the GlcNAcTr I, galactosyltransferase and sialyltransferase exemplified herein, catalyze the transfer of a monosaccharide from a high-energy sugar donor to an acceptor oligosaccharide. The generalized reaction is: sugar nucleotide+acceptor=>acceptor sugar+ nucleotide.

To follow the reaction in vitro, a sugar nucleotide can be provided in a form that will label the acceptor. For example, the specific activity of the commercial radiolabelled sugar nucleotides is sufficiently high to allow detection of fmoles of acceptor substrate in a radiolabelled assay.

Neither glycosyltransferases nor the sugar nucleotide substrates are permeable to cell membranes. This allows the extracellular alteration of cell surface glycosylation on intact cells or sealed membrane preparations, using the method of the invention in those embodiments wherein the GlcNAc Tr I reaction does not occur within the host cell.

GlcNAcTr I (EC 2.4.1.101) is the medial Golgi transferase that initiates complex N-linked carbohydrate formation. This enzyme is also known as UDP-N-acetylglucosamine:α-3-D-mannoside β 1,2-N-acetylglucosaminyltransferase I. The human gene encoding this enzyme has been cloned and its coding sequence published (Kumar, R. et al., *Proc. Natl. Acad. Sci., USA* 87:9948–9952 (1990). Other GlcNAc Tr I sources include rabbit (Sarkar, M. et al., *Proc. Natl. Acad. Sci. USA* 88:234–238 (1991) and mouse (Kumar, R. et al., *Glycobiology* 2:383–393 (1992)).

Other enzymes useful in the construction of the hybrid oligosaccharide, as shown in FIG. 1, are also available and have been cloned. For example, a non-limiting list includes bovine β(1,4)galactosyl transferase (D'Agostaro, G. et al., *Eur. J. Biochem.* 183:211–217 (1989), human β(1,4) galactosyl transferase (Masri, K. A. et al., *Biochem. Biophys. Res. Commun.* 157:657 (1988), rat α(2,6)sialyltransferase (Wang, X. C. et al., *Glycobiology* 1:25–31 (1990), and rabbit α1,2 mannosidases (Lal, A. et al., *J. Biol. Chem.* 269:9872–9881 (1994)) or with mouse α1-2 mannosidases (Herscovics, A. et al., *J. Biol. Chem.* 269:9864–9871 (1994).

To clone a reported sequence, primers may be designed based upon the reported sequence. For example, primers such as those of SEQ ID No: 1 and SEQ ID No: 2 can be used to amplify the coding sequence of human GlcNAc Tr I, for example, using PCR techniques, so as to insert such coding sequence into any vector of choice, and preferably an expression vector capable of expression of such coding sequence in a desired host.

The GlcNAc Tr I enzyme is not glycosylated. Mouse GlcNAc Tr I has been expressed by Kumar, R. et al., *Glycobiology* 2:383–393 (1992). It is possible and useful to express mouse and human GlcNAc Tr I intracellularly in bacteria, but it may form protein aggregates. For this reason, intracellular production in bacteria is not the preferred method for the production of GlcNAc Tr I. The enzyme can be produced in mammalian cells such as COS cells, be secreted into the medium, and used directed in that medium if desired; it should be noted that use of the enzyme in the spent growth medium is simply for convenience; the cell's growth medium environment is not necessary per se for GlcNAc Tr I activity as the enzyme produced in bacteria was active. Isolation methods for the enzyme from rabbit liver are also known (Nishikawa, Y. et al., *J. Biol. Chem.* 263:8270–8281 (1988)).

In the methods of the invention, GlcNAcTr I reactions are preferably run at 37° C. One unit is that enzyme activity that catalyzes transfer of 1 μmol GlcNAc from UDP-GlcNAc to Man₅GlcNAc within 1 minute at 37° C. and pH 6.1. As exemplified, 330 μmol acceptor substrate and 340 umol UDP-GlcNAc were used with 10–15 μl of a 10-fold concentrated COS supernatant (containing about 30 microunits GlcNAc Tr I in a reaction mixture with a final volume of 30 μl. One unit of enzyme activity converts 1 μmol substrate in one minute. Reaction times will vary depending upon the concentration and specific activity of the enzyme, but generally 5–10 hours, and, as exemplified, 1–4 hours, are sufficient for the purposes of the methods of the invention. The GlcNAc Tr I reaction can be run for a longer time as the scale of the reaction is increased (Ichikawa et al., *Anal. Biochem.* 202:215–238 (1992)).

The enzymes do not need to be pure to be useful, as exemplified using the COS cell medium as a source of GluNac Tr I. However, large scale isolation of the glycosyltransferases can be achieved using nucleotide-affinity adsorbents as known in the art. The glycosyltransferase may be modified by the addition of an affinity tag (such as the streptavidine-tag or a histidine-tail) in order to enhance purification and reduce purification costs.

β-1,4 Galactosyl transferase, EC 2.4.1.38, such as that from human milk exemplified herein, is commercially available from Boehringer Mannheim (catalog no. 1088-696), and Sigma Chemical Co., St. Louis, Mo. Its purification from bovine milk was reported by Barker, R. et al., *J. Biol. Chem.* 247:7135 (1972). In the presence of α-lactalbumin, EC 2.4.1.38 becomes EC 2.4.1.22, lactose synthetase (also known as lactose synthase and UDP-D-galactose: D-glucose4β-galactosyltransferase), and accepts glucose as a substrate for the transfer of galactose to produce lactose (Yoon et al., *Glycobiology* 2:161–168 (1992)). This enzyme is commercially available from Sigma and Oxford Glycosystems. It is also easy to purify (Barker, R. et al., *J. Biol. Chem.* 247:7135 (1972)). Bovine galactosyl transferase can be used in the same way and under the same reaction conditions as that from human. Cloned β-1,4 galactosyl transferase has been expressed in several systems (see, Masibay, A. et al., *Proc. Natl. Acad. Sci. USA* 86:5733–5737 (1989), Aoki, D. et al., *EMBO J.* 9:3171 (1990) and Krezdorn, C. et al., *Eur. J. Biochem.* 212:113–120 (1993)).

The enzymatic reaction conditions of β-1,4 Galactosyl transferase, EC 2.4.1.38, are known in the art (Parchment, R. E. et al., *Anal. Biochem.* 154:460–469 (1986); Nunez, H. and Barker, R., *Biochemistry* 19:489–495 (1980)). The enzyme requires a pH of 8–8.5 and 1–50 mM manganese, preferably 20 mM, for optimal enzymatic activity. Reactions are preferably run at 37° C., with about 65 mU enzyme and 5 μmol UDP-galactose per ml. One unit of enzyme activity is the enzyme activity that catalyzes transfer of 1 μmol galactose from UDP-galactose to glucose in the presence of α-lactalbumin, in 1 minute at 37° C. and pH 8.4. However, for commercially available galactosyl transferase (5.5 units per mg), in the absence of α-lactalbumin and with GlcNAc as the substrate, the enzymatic activity may be reduced, for example, to about 3.5 U/mg. Reaction times will vary depending upon the concentration and specific activity of the enzyme, but generally 6–10 hours for small scale, and, as exemplified, 8 hours, are sufficient for the purposes of the methods of the invention. Longer times may be necessary as the scale of the reaction is increased.

α-2,6 Sialyltransferase, EC 2.4.99.1, such as that from rat liver exemplified herein, is commercially available from Boehringer Mannhein (catalog no. 981-583), and from Genzyme, Calbiochem, and Sigma. Its purification was reported by Weinstein, J. et al., *J. Biol. Chem.* 257:13, 835–13,844 (1982). The enzyme is also known as CMP-N-acetylneuraminite:β-D-galactosyl-1,4-N-acetyl-β-D-glucosamine α-2,6-N-acetylneuraminyltransferase. The $K_m$ for the sugar donor CMP-NeuAc is $8.5 \times 10^{-5}$M. The acceptor sequence is Galβ1,4GlcNAc-R. Purification methods for sialyltransferases involved in N-glycosyl synthesis are known (Weinstein, J. et al., *J. Biol. Chem.* 262:17735–17743 (1987)). Recombinant production of sialyltransferases has been reported in mammalian COS and CHO cells (Schachter, H. et al., in "Molecular Glycobiology," Fukuda, M. et al., eds., IRL Press, pp. 88–162 (1994). The cloning of human α-2,6 sialyltransferase was reported in Grundmann, U. et al., *Nucleic Acids Res.* 18:667 (1990).

One unit of α-2,6 sialyltransferase will transfer 1 μmol N-acetylneuraminic acid from CMP-N-acetylneuraminic acid to asialo-α₁-glycoprotein in 1 minute at 37° C. (Weinstein, J. et al., *J. Biol. Chem.* 257:13835–13844 (1982) ). The enzyme requires a pH of 6–6.5 for optimal activity, and 50 mM NaCl is generally added to the assay to stabilize the enzyme's activity. Reactions are preferably run at 37° C., with about 4–40 mU enzyme, 0.5–5 μmol CMP-NANA per ml (100–800 μg acceptor protein per ml were used in the exemplified embodiments), and preferably 3.6 µmol. Reaction times will vary depending upon the concentration and specific activity of the enzyme, but generally 6–10 hours for small scale syntheses, and longer for large scale application, are sufficient for the purposes of the methods of the invention.

α1,2 Mannosidase (EC 3.2.1.24), such as that from *Aspergillus saitoi* exemplified herein, is commercially available from Oxford Glycosystems, Oxford, UK. One unit of enzyme is the amount of enzyme that will release one µmole of mannose from bakers yeast mannan per minute at pH 5.0 and 37° C. In the exemplified embodiments, 6 µunits enzyme were used to treat up to 500 µg protein in a 30 µl final volume, and 2 µunits enzyme were used to treat about 5 µg bovine ribonuclease B oligosaccharides (Oxford GlycoSystems Cat No. RP-2500) in 10 µl final volume. Preferably the pH is about 5.0 for optimal activity of the enzyme from *A. saitoi*. Reactions are preferably run at 37° C.

Methods for detection of the products of these reactions are well known and exemplified herein.

IV. Modification of Glycosylation Patterns

According to the invention, the modification of glycoproteins may be effected in vitro by carbohydrate modifying enzymes described above that are capable of synthesizing or modifying glycosylation structures. Glycoproteins synthesized by yeast, filamentous fungi and insect cells, can be structurally and functionally dissimilar to mammalian-type carbohydrate structures in having a high mannose or hybrid-type character. However, as embodied by this invention, these high mannose oligosaccharide structures can be enzymatically converted into hybrid or complex structure, making the carbohydrate structure on the yeast, fungi, or insect produced protein more similar to, or identical to, the mammalian-produced carbohydrate structure.

It has been surprisingly discovered that filamentous fungi such as, for example, Trichoderma, unlike yeast, synthesize glycoproteins in an form that is recognizable as an acceptor substrate for the enzyme N-acetylglucosaminyl transferase I (GlcNAc Tr I), especially human GlcNAc Tr I. This form is an "immature" mammalian form.

However, GlcNAc Tr I is not naturally present in these hosts. According to the invention, the above finding is exploited such that the glycosylation pattern of a desired glycoprotein, for example, a recombinant protein that was produced in Trichoderma, having a structure that can serve as an acceptor substrate for GluNac Tr I, for example, formula (IV) above, is modified by a cascade of sequential reactions, for example three sequential reactions with the following enzymes: first, GlcNAc Tr I; second, β-1,4 galactosyl transferase; and third, α-2,6 sialyltransferase. The result of this cascade is the production of a glycoprotein having at least a hybrid glycosylation pattern, and, when all branch termini are modified, a complex-type glycosylation pattern. Such branches are preferably terminated with terminal sialic acid units, similar to that of mammalian cells, although, as desired other terminal units can be used, such as those described earlier.

As described below, a recombinant host can be prepared such that the first reaction, that of GlcNAc Tr I, is performed in vivo, in the host, prior to secretion of the protein.

It has also been surprisingly found that treatment of glycoproteins that have been synthesized by yeast and Trichoderma, with mannosidase, so as to trim (remove) mannose residues from such glycoprotein, provides (in the case of yeast) or enhances (in the case of Trichoderma), acceptor substrate sites for GlcNAc Tr I enzymatic action. According to the methods of the invention, a mannosidase may be used to pretreat the acceptor substrate prior to reaction with GlcNAc Tr I, to create, or otherwise enhance the availability of, target sites of GlcNAc Tr I action on such substrate.

Therefore, in a first embodiment, GlcNAc Tr I activity is used to convert an acceptor substrate of a high mannose type to a hybrid-type. The hybrid type can then be converted to a different hybrid type, or, a complex type. In a highly preferred embodiment, the source of the acceptor substrate for GlcNAc Tr I is a glycoprotein that has been produced in a filamentous fungi, and especially Trichoderma, and most especially *T. reesei*.

It is not necessary to extract the product of each reaction from the mixture prior to starting the subsequent reaction. The pH and assay conditions (such as the addition of divalent cations) can simply be adjusted in the same container for each subsequent reaction so that handling is minimized. Additionally, solid state technology can be used to provide the enzymes on a solid support and the acceptor substrate simply passed through such support or the solid support can be used in batch form.

The glycoprotein source of the acceptor substrate can be the native or recombinant glycoprotein product of any host that provides such glycoprotein in useable form. Especially, the glycoprotein is a native or recombinant product of a filamentous fungi, for example, a member of the genera Absidia, Acremonium, Alternaria, Aspergillus, Aureobasidium, Beauveria, Ceratocystis, Chaetomium, Cladosporium, Collectotrichum, Fusarium, Gliocladium, Mortierelia, Mucor, Paecilomyces, Penicillium, Phanerochaete, Phytophthora, Pythium, Rhizopus, Trichoderma, and Verticillium. Most especially, the host is a member of the Aspergillus or Trichoderma genera.

Trichoderma species useful as hosts for the production of substrate acceptors of GlcNAc Tr I include *T. reesei*, such as QM6a, ALKO2442 or CBS383.78 (Centraalbureau voor Schimmelcultures, Oosterstraat 1, PO Box 273, 3740 AG Baarn, The Netherlands, or, ATCC13631 (American Type Culture Collection, 12301 Parklawn Drive, Rockville, Md., 10852, USA, type); *T. viride* (such as CBS189.79 (det. W. Gams); *T. longibrachiatum*, such as CBS816.68 (type); *T. pseudokoningii* (such as MUCL19358; Mycothèque de l'Université Catholique de Louvain); *T. saturnisporum* CBS330.70 (type); *T. harzianum* CBS316.31 (det. W. Gams); *T. virgatum* (*T. pseudokoningii*) ATCC24961. Most preferably, the host is *T. reesei* and especially *T. reesei* strains QM9414 (ATCC 26921), RUT-C-30 (ATCC 56765), and highly productive mutants like VTT-D-79125, which is derived from QM9414 (Nevalainen, Technical Research Centre of Finland Publications 26, (1985), Espoo, Finland). The transformation of Trichoderma may be performed by any technique known in the art, including the technique taught in European patent application EP 244,234.

Preferred species of Aspergillus that are useful hosts in the methods of the invention include *A. nidulans, A. awamore* and *A. niger*. Methods for the transformation of Aspergillus are known.

As described below, when pretreated in vitro with α1,2 mannosidase, yeast such as *Pichia spp.* (especially *Pichia pastoris*), *Hansenula spp.* (especially *Hansenula polymorpha*), *Kluyveromyces lactis, Yarrowia lipolytica*, or *S. cerevisiae* are useful hosts for expressing a gene of interest. Yeast would be useful as a host for expressing cloned GlcNAc Tr I enzyme since it is not glycosylated.

In one embodiment, the glycoprotein acceptor substrate is secreted into the growth medium of the production host and is modified in vitro by the action of enzymes such as GlcNAc Tr I without being removed from such medium. If desired, the medium can be concentrated prior to enzymatic modification of the gene of interest. Alternatively, the glycoprotein acceptor substrate can be provided to the GlcNAc Tr I in a purified or isolated form.

In a preferred embodiment of the invention, the coding sequence of GlcNAc Tr I is transformed into a desired host cell from which it is also desired to synthesize the protein of interest, especially, a host cell that does not naturally catalyze the enzymatic modifications according to the methods of the invention. In this embodiment, the first step in the modification of glycosylation pattern, the reaction catalyzed by GlcNAc Tr I is effected in vivo. The host cell then synthesizes, and preferably secretes, an acceptor substrate of a hybrid type. The hybrid type is then converted to a hybrid type that contains terminal sialic acids by the second and third steps of the cascade in vitro, that is, the addition of galactose residues with β-1,4 galactosyl transferase, followed by the addition of sialic acid residues with α-2,6-sialyltransferase.

Preferably, the recombinant host that is transformed with both GlcNAc Tr I coding sequences and, if desired, with the coding sequence for a protein of interest (the glycosylation pattern of which is to be modified in vivo by the action of the expressed GlcNAc Tr I), is a member of the Aspergillus or Trichoderma genera as described above.

Vector systems are known that are useful in transforming hosts, especially the Aspergillus or Trichodenna hosts described above for the production of the GlcNAc Tr I and glycoproteins of the invention. A separate vector may be used to provide the selectable marker.

Expression of genes in a host requires the use of regulatory regions functional in such hosts. A wide variety of transcriptional and translational regulatory sequences can be employed; filamentous fungi such as Trichoderma generally recognize eukaryotic host transcriptional controls, such as, for example, those of other filamentous fungi, and especially, Aspergillus.

In a preferred embodiment, genetically stable transformants of Trichoderma are constructed whereby DNA encoding a desired glycoprotein or carbohydrate modifying enzyme like GlcNAc Tr I is integrated into the Trichoderma host chromosome. The coding sequence for the desired glycoprotein or enzyme may be from any source. Such integration may occur de novo within the cell or, in a most preferred embodiment, be assisted by transformation with a vector which functionally inserts itself into the host chromosome, for example, DNA elements which promote integration of DNA sequences in chromosomes.

After the introduction of the vector, recipient cells are grown in a selective medium, which selects for the growth of the transformed cells. Expression of the cloned gene sequence(s) results in the production of the desired glycoprotein and/or carbohydrate modifying enzyme, or in the production of desired fragments thereof. This expression can take place in a continuous manner in the transformed cells, or in a controlled manner, for example, wherein expression is the result of a regulated promoter.

In a preferred embodiment, a desired glycoprotein or carbohydrate modifying enzyme is secreted into the surrounding medium due to the presence of a functional secretion signal sequence, preferably a signal homologous to the host. If a desired gene does not code for a signal sequence, or if its signal sequence does not function well in the host, then the glycoprotein's coding sequence may be operably linked to another signal sequence, either homologous or heterologous to the host, that functions in such host. The desired coding sequence may be linked to any signal sequence which will allow secretion of the glycoprotein from the selected host, for example, for secretion from Trichoderma, the signal sequence of the Trichoderma cellulase enzymes may be used, for example, the secretion signal of the cellobiohydrolase I (CBHI) cellobiohydrolase II (CBHII), endoglucanase I (EGI) or endoglucanase II (EGII) protein may be used. Secretion signals of the Trichodenna xylanases are also useful. Such signal sequences may be designed with or without specific protease sites such that the signal peptide sequence is amenable to subsequent removal.

In those embodiments wherein GlcNAc Tr I is provided intracellularily within the fungal host cell so as to act on a substrate intracellularly, it is not necessary, and not preferable, to secrete recombinantly produced GlcNAc Tr I into the medium as it is necessary that it remain in the host cell to be active in vivo in those embodiments.

Trichodenna is an especially useful and practical host for the synthesis of the glycoproteins of the invention because Trichoderma is capable of secreting protein in large amounts, for example, concentrations as high as 40 g/L culture medium have been reported; the homologous cellulase and hemicullulase promoters such as the Trichodenna cbh1, cbh2, egl1 and egl1 promoters provide very convenient promoters for the high expression of genes of interest because they are strong promoters. For example, the cbh1 promoter is a single copy promoter that normally directs the synthesis of up to 60% of the secreted protein from the Trichodenna host. Alternatively, the gene of interest, or the GlcNAc Tr I gene, can be inserted into the CBHI locus. The Trichodenna transformation system is highly versatile and can be adapted for any gene of interest. Culture of Trichoderma is supported by previous extensive experience in industrial scale fermentation techniques; for example, see Finkelstein, D. B. et al., eds., *Biotechnology of Filamentous Fungi: Technology and Products*, Butterworth-Heinemann, publishers, Stoneham, Mass. (1992).

V. Proteins of Interest

The methods of the invention are useful with any desired protein of interest that contains high mannose-type glycosylation patterns. Such patterns are considered to be "immature" when compared to complex or hybrid patterns.

Especially, a protein of interest may be a protein, such as an immunoglobulin or hormone, that is to be provided to a patient in need of same, especially for therapeutic reasons. Examples of glycohormones wherein glycosylation plays a role in the properties of such hormone, especially the therapeutic properties, include erythropoietin (EPO), human choriogonadotropin (HCG), follitropin (FSH), thyrotropin (TSH) and lutropin (LH). Modification of each peptide subunit according to the methods of the invention may be performed. Examples of other proteins of interest whose biosynthesis, transport or function are altered by N-glycosylation include NCAM, tenascin, thrombospondin, fibronectin, hormones, cytokines, (especially interleukin-4 and interferon gamma), growth factors, plasma proteins, coagulation factors, soluble receptors, immunoglobulins (antibodies), granulocyte-macrophage colony stimulating factor (GM-CSF), vascular endothelial growth factor, HIV virus glycoprotein gp120, viral coat proteins, immunoglobulin D, antithrombin IIIβ, plasminogen, von Willebrand factor, fibrinogen, corticosteroid-binding globulin, thyroxine-binding globulin, folate-binding protein, fibrinectin, bone and platelet osteonectin, EGF receptor, insulin and insulin-like growth factor-I receptors, basic fibroblast growth factor receptor, lymphocyte CD2, MHC Class II molecules, glucose transporters, erythrocyte band 3 protein, β-2 adrenergic receptors, transferrin receptor, VIP receptor, membrane class I MHC protein, vasopressin receptor of LLC-PK1 cells, low density lipoprotein receptor, asialoglycoprotein receptor, CD4 protein, thyrotropin receptor, PDGF receptor, jack bean concanavalin A, cobra venom factor, lactotransferrin, spinach chloroplast coupling factor, submaxillary gland mucin, intestinal brush border lactase-phlorizin hydrolase, arctic fish antifreeze glycoprotein, LDL receptor, glucophorin A, and β-HCG, and, generally, secreted animal proteins and plant glycoproteins secreted by sycamore cells in culture. Especially, those proteins that require targetting to specific organs or cells through sugar-lectin recognition are useful protein substrates for modification of glycosylation patterns according to the invention.

The method of the invention is especially useful in designing a protein for use in genetic therapy; in such therapy, a protein, such as an enzyme, that is deficient in a cell or organ, is targeting to such cell or organ by providing such protein with an appropriate glycosylation pattern.

VI. Preparation of Modified Glycoproteins as Pharmaceutical Compositions

According to this invention, there is provided a method for producing high levels of glycoproteins which are desirable for use, for example, in pharmaceutical compositions. Such glycoproteins may be obtained directly from the hosts of the invention or the culture medium. Further, if desired activities are present in more than one recombinant host (such as multisubunit proteins), such preparations may be isolated from the appropriate hosts and combined prior to use in the method of the invention; alternatively one host can be used to make all subunits of the desired protein.

To obtain the glycoprotein preparations of this invention, the recombinant hosts described above which have the desired properties (that is, hosts capable of expressing the glycoproteins) are cultivated under suitable conditions, the modified glycoproteins are secreted from the Tnichodenna hosts into the culture medium, and the glycoproteins are recovered from the culture medium by methods known in the art. Alternatively, but less desirably the glycoproteins can be recovered from the host cells themselves.

The glycoprotein is recovered from the culture medium or host cells themselves by using routine methods which are well known in the art. The glycoprotein of the invention may be lyophilized or the glycoprotein otherwise concentrated and/or stabilized for storage. The glycoprotein of the invention are very economical to provide and use. If the glycoproteins are secreted into the culture medium, only the culture medium need be recovered to obtain the desired glycoprotein; there is no need to extract an glycoprotein from the Trichoderma hosts unless it is no desire to do so.

If desired, an expressed glycoprotein may be further purified in accordance with conventional conditions, such as extraction, precipitation, chromatography, affinity chromatography, electrophoresis, or the like.

The methods of the invention provide for the manufacture of hybrid or complex glycosyl groups on recombinant glycoproteins for their use as pharmaceutical agents in a safer and more cost-effective manner than is currently available. The methods of the invention also provide an important benefit in that they result in the synthesis of uniform and well-defined glycosyl structures. Production of a single glycoform can be critical if it is desired to obtain uniform therapeutic pharmacokinetic profiles.

As would be understood by one of ordinary skill in the art, the pharmaceutical compositions of the present invention can be formulated according to known methods to prepare such compositions, whereby the glycoproteins with mammalian-type oligosaccharides are combined with a pharmaceutically acceptable excipient. Suitable excipients and their formulation are described, for example, in *Remington's Pharmaceutical Sciences* (18th ed., Gennaro, A. R., ed.), Mack Publishing Co., Easton, Pa. (1990); see especially Part 4, "Testing and Analysis," pp. 435–602, and Part 8, "Pharmaceutical Preparations and Their Manufacture," pp. 1435–1712). In order to form a pharmaceutically acceptable composition suitable for effective administration, such compositions may additionally contain an effective amount of salts, buffers, adjuvants or other substances which will improve the efficacy of the composition.

Pharmaceutical methods may be employed to control the duration of action. Controlled release preparations may be achieved through the use of polymers to complex or absorb the compositions of this invention, their equivalents, or their functional derivatives. The controlled delivery may be exercised by selecting appropriate macromolecules (for example polyesters, polyamino acids,polyvinyl, pyrrolidone, ethylenevinylacetate, methylcellulose, carboxymethylcellulose, or protamine sulfate) and the concentration of the macromolecules as well as the methods of incorporation in order to control release. Another method to control release is to incorporate the compositions of the invention into particles of a polymeric material such as polyesters, polyamino acids, hydrogels, poly(lactic acid) or ethylene vinylacetate copolymers. Alternatively, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences, supra.

The pharmaceutical compositions of the present invention can also be formulated for administration orally, or parenterally by injection (for example by subcutaneous, intramuscular or intravenous injection), by intravenous or other infusion, by nasopharyngeal absorption (intranasopharangeally), percutaneously, rectally, ocularly or sublingually. Compositions for parenteral administration may include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Carriers, adjuncts or occlusive dressings can be used to increase skin permeability and enhance absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include wetting agents, emulsifying and suspending agents, or sweetening, flavoring, coloring or perfuming agents.

In one embodiment, the pharmaceutical compositions of the present invention may be formulated as a cream, lotion, ointment, or the like, for topical administration to the skin. Such compositions may optionally contain wetting agents, emulsifying and suspending agents, or coloring or perfuming agents.

A composition is said to be "pharmacologically acceptable" if its administration can be tolerated by the recipient without the production of serious side effects. Such an agent is said to be administered in a therapeutically "effective" amount or concentration if it produces the desired biologic effect(s).

Generally, the dosage needed to provide an effective amount or concentration of the composition can be adjusted by one of ordinary skill in the art, such as a medical doctor, and will vary depending upon such factors as the route of administration and the recipient's age, condition, sex, and extent of disease, if any, and other variables.

The recipient of the proteins modified according to the methods of the invention can be any animal into which it is desired to administer such protein, including humans, zoo animals, farm animals (bovine, ovine and the like), and pets (cats, dogs, birds, etc.).

The invention is described in more detail in the following examples, These examples show only a few concrete applications of the invention. It is self-evident for one skilled in the art to create additional similar applications and embodiments thereof. Hence the examples should not be interpreted to narrow the scope of the invention but rather only to clarify the use of the invention.

EXAMPLES

Example 1

Preparation of *Trichoderma reesei* Glycoproteins

Glycoproteins from the *T. reesei* mutant strain RUTC 30 were obtained after growth in a minimal medium for the induction of cellulases (Uusitalo et al., *J. Biotechn.* 17:35–50 (1991)). As carbon sources for growth, lactose or a combination of lactose/cellulose (2% final concentration) were added. The method of Bradford, M. M. (*Anal. Biochem.* 72:248–254 (1976)) was used to measure the concentration of the proteins with immunoglobulin G as a standard. For glycosyltransferase experiments, the secreted proteins were subsequently dialyzed against the proper buffer used in the subsequent glycosyltransferase assay. A fast change to the new buffer was possible without significant loss of the proteins when using Microcon™ ultracentrifugation devices (Amicon) (Blatt et al., *Anal. Biochem.* 26:151–173 (1968)). A mixture of cellulases from a second, unknown strain of *T. reesei* were commercially obtained from Fluka Chemie, Buchs, Switzerland.

Example 2

Preparation of Oligosaccharides

Oligosaccharides were prepared according to a method described by Verostek et al. (*Glycobiology* 2:458 (Abstract 1.06) (1992)). Oligosaccharides were released from the glycoproteins (1–20 mg/ml) by recombinant PNGase F (Tarentino et al., Biochem. 24:4665–4671 (1985)) (Biolabs). Glycoproteins were first dissolved in 50 mM sodium phosphate (pH 7.5), 0.5% SDS and 1% β-mercaptoethanol, or in 50 mM Tris-HCl, pH 7.0. The proteins were then denatured by boiling for 10 minutes. The nonionic detergent nonidet P-40™ was added to prevent the inhibition of PNGase F by SDS. The reaction mixture was incubated with 1000 units PNGase F at 37° C. for 18 hours. After PNGase F treatment, the proteins and oligosaccharides were precipitated by adding four volumes of acetone at minus 20° C. The 80% acetone salt- and SDS-containing supernatant was discarded, and the pellet was extracted twice with ice cold 60% methanol. Methanol was removed from the pooled supernatants after lyophilization by evaporation. Further purification of the oligosaccharides was obtained by passage through a Bio-Gel P2™ column (27 cm high, 0.5 cm diameter; obtained from BIORAD). The presence of oligosaccharides in the different collected fractions was traced through orcinol staining (*Révélateurs pour la chromatographie en couche mince et sur papier*, Merck, p. 91 (1980)). In a second round, pooled oligosaccharide-containing fractions were passed over a Bio Gel P2™ (Biorad) column to obtain oligosaccharides that were sufficiently pure to use in the glycosyltransferase assays.

Example 3

Amplification of GlcNAc Tr I Genomic DNA Sequence

Figure 2:
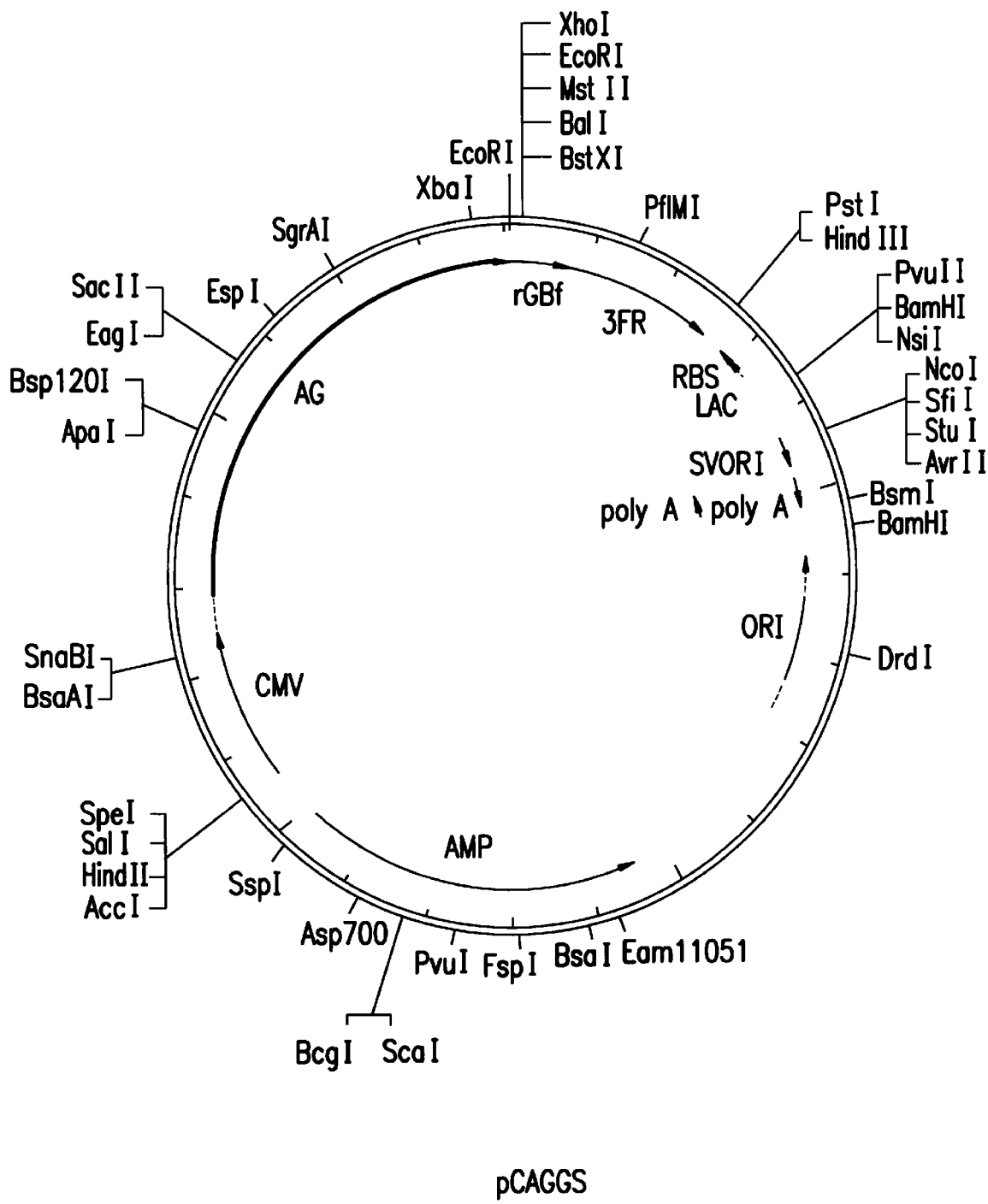
FIG. 2.

The coding region of the GlcNAc Tr I gene (Genbank Accession No. M55621; EMBL Accession No. HSGLCNAC; Kumar et al., *Proc. Natl. Acad. Sci. USA* 87:9948–9952 (1990); all incorporated herein by reference;) from colon carcinoma genomic DNA was amplified using PCR and was subsequently cloned into the mammalian expression-vector pCAGGS (FIG. 2 and described in Niwa et al., *Gene* 108:193–200 (1991)). The human colorectal adenocarcinoma cell line DLD-1 was used as the source of genomic DNA. This cell line is available from the American Type Culture Collection, Rockville, Md., (ATCC CCL 221) and is described in *Cancer Research* 39:1020–1025 (1979)). Plasmid pCAGGS was the gift of J. Miyazaki, Univ. Tokyo, Japan. Plasmid pCAGGS is useful for highly efficient expression of genes under the control of the β-actin/β-globin hybrid promoter and CMV-IE enhancer in various mammalian cells. pCAGGS carries a modified chicken β-actin promoter: the splice acceptor sequence of the β-actin promoter region is replaced by a rabbit β-globin fragment containing a 3' part of the second intron and a 5' part of the third exon. The resulting β-actin/β-globin hybrid promoter is designated the "AG" promoter.

Genomic DNA was prepared from colon cells, according to the procedure described by Maniatis, T., "Molecular Cloning, A Laboratory Manual," 2nd edition, Sambrook et al., eds., Cold Spring Harbor Press, Cold Spring Harbor, 1989. A genomic DNA fragment representing the coding region of the GlcNAc Tr I gene was amplified with *Pyrococcus furiosus* polymerase (Stratagene) and a Pharmacia thermal cycler according to the instructions of the manufacturer. The N-terminal oligonucleotide primer consisted of the sequence:

5'-CCAGGATGCTGAAGAAGCAGTCTGCA-3' (SEQ ID NO:1).

The C-terminal oligonucleotide primer consisted of the sequence:

5'-CCAGTCGACAGGTGCTAATTCCAGCTAG-3' (SEQ ID NO:2).

The amplification protocol consisted of an initial denaturing cycle of 8 minutes at 96° C., followed by a 1 minute annealing step at 65° C. and finally a 4 minute polymerization cycle at 75° C. The amplification then switched to a 1 minute denaturation, 1 minute annealing and a 4 minute polymerization for 24 additional cycles.

Example 4

Subcloning the Polymerase Chain Reaction (PCR)-Generated Fragments

A fraction of the PCR fragments has a single adenosine nucleotide added at the 3' end because of the template-independent terminal transferase activity of *Pyrococcus furiosus* polymerase. This activity was exploited to clone the amplified DNA fragments with the efficiency of sticky end cloning. To do this, the pUC18 vector (into which the fragment would be linked) was prepared as follows. One μg Hind II-digested vector was incubated with 20 units of terminal transferase and 10 μM ddTTP in a final volume of 30 μl for 1 hour at 37° C. ddTTP was used to assure the incorporation of only one thymidine at the 3' ends of the blunt digested vector (Holton et al., *Nucleic Acids Research* 19(5):1156 (1990)). The vector and the PCR fragments were purified using the Gene Clean™ kit from Pharmacia. The amplified GlcNAc Tr I coding fragment (200 ng) was finally ligated in the pUC18 vector (40 ng) at 12° C. for 17 hours. The first part of the gene (MLKKQSA- GLVLWGAIL- FVAWNALLLLFFWTRPAPGRPPSVS [SEQ ID NO:3]) which coded for secretion and for retention in the medial Golgi compartment was replaced with a nucleotide sequence coding for the "prepro"—secretion signal-sequence of the yeast mating factor. This nucleotide-sequence was isolated from the plasmid pSCGAL1MF3 (Belgian Coordinated Collections of Microorganisms (BCCM) catalogue of the Laboratorium voor Moleculaire Biologie Plasmidencollectie (LMBP) culture collection at University Gent) after digestion with Stu I and Xba I restriction enzymes. (Materials listed as being obtained from the LMBP are available to anyone who requests them). The yeast mating factor nucleotide sequence that was used is Essentially, the XbaI-StuI fragment of pSCGAL1MF3 (above), containing the prepro secretion signal of the α-mating factor 1 gene, was ligated to the XbaI-Eco47III vector fragment of pUChGNTI. Because of the template-independent terminal transferase activity of *Pyrococcus furiosus* polymerase, a fraction of the PCR fragments has a single adenosine nucleotide added at the 3' end. We exploited this activity to clone the amplified DNA fragments with the efficiency of sticky end cloning. To do this, the acceptor pUC18 vector was prepared as follows: 1 μg Hind II digested vector was incubated with 20 units terminal transferase and 10 μM ddTTP in a final volume of 30 μl for 1 hour at 37° C. (Holton and Graham, 1990). The amplified GlucNAc Tr I coding fragment (200 ng) was ligated in the treated pUC18 (Norrander et al., *Gene* 26:101–106 (1983) vector (40 ng) at 12° C. for 17 hours. This intermediate construct was then digested with HindIII and EcoRI, the sticky ends were filled in with Klenow DNA polymerase and EcoRI linkers (5'-CGGAATTCCG-3') were added. Finally, this EcoRI-EcoRI fragment was digested with XbaI and EcoRI and the resulting XbaI-EcoRI fragment was inserted into the XbaI-EcoRI digested pCAGGS vector. This expression plasmid carries a fusion of the prepro secretion signal of the α-mating factor 1 gene to the mature human gene encoding N-acetylglucosaminyltransferase I (GlcNAc Tr I), coded into the sense orientation relative to the chicken β-actin promoter that is preceded by the CMV-IE enhancer sequence. The nucleotide sequence of the human GlcNAc Tr I was obtained from EMBL Accession no. M55621.

| ATG | AGA | TTT | CCT | TCA | ATT | TTT | ACT | GCA | GTT | TTA | TTC | GCA | GCA | TCC | TCC |
|-----|-----|-----|-----|-----|-----|-----|-----|-----|-----|-----|-----|-----|-----|-----|-----|
| MET | Arg | Phe | Pro | Ser | Ile | Phe | Thr | Ala | Val | Leu | Phe | Ala | Ala | Ser | Ser |
| GCA | TTA | GCT | GCT | CCA | GTC | AAC | ACT | ACA | ACA | GAA | GAT | GAA | ACG | GCA | CAA |
| Ala | Leu | Ala | Ala | Pro | Val | Asn | Thr | Thr | Thr | Glu | Asp | Glu | Thr | Ala | Gln |
| ATT | CCG | GCT | GAA | GCT | GTC | ATC | GGT | TAC | TCA | GAT | TTA | GAA | GGG | GAT | TTC |
| Ile | Pro | Ala | Glu | Ala | Val | Ile | Gly | Tyr | Ser | Asp | Leu | Glu | Gly | Asp | Phe |
| GAT | GTT | GCT | GTT | TTG | CCA | TTT | TCC | AAC | AGC | ACA | AAT | AAC | GGG | TTA | TTG |
| Asp | Val | Ala | Val | Leu | Pro | Phe | Ser | Asn | Ser | Thr | Asn | Asn | Gly | Leu | Leu |
| TTT | ATA | AAT | ACT | ACT | ATT | GCC | AGC | ATT | GCT | GCT | AAA | GAA | GAA | GGG | GTA |
| Phe | Ile | Asn | Thr | Thr | Ile | Ala | Ser | Ile | Ala | Ala | Lys | Glu | Glu | Gly | Val |
| TCT | TTG | GAT | AAA | AGG | [Seq ID NO:4] | | | | | | | | | | |
| Ser | Leu | Asp | Lys | Arg | | | | | | | | | | | |

Figure 3:
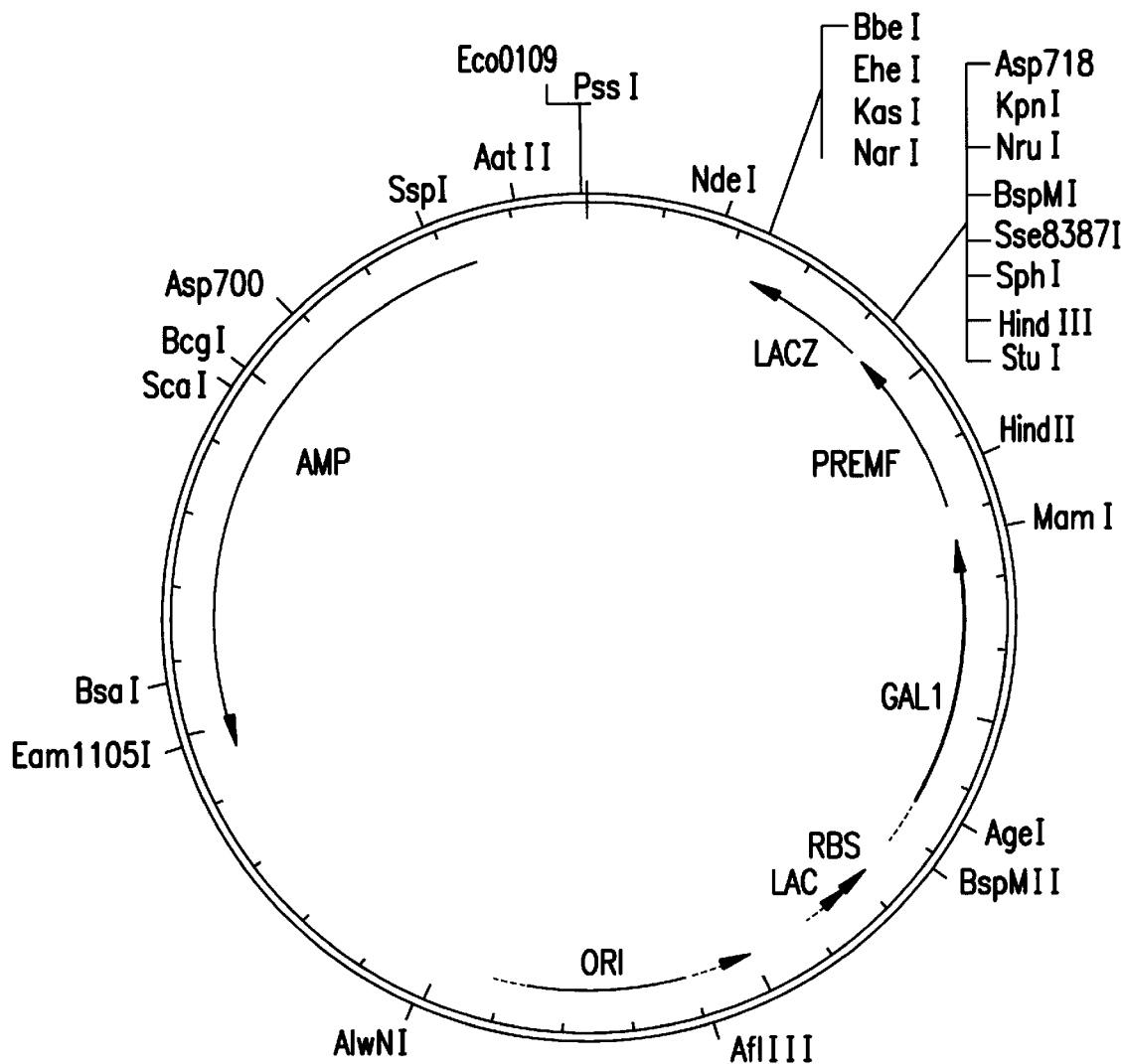
FIG. 3.

A map of plasmid pSCGAL1MF3 appears as FIG. 3.

To make plasmid pSCGAL1MF3, plasmid pSCGAL1MF2 (available from the LMBP collection) was opened with AccI, filled in with Klenow DNA polymerase and ligated. In this way, the HindII and SalI sites of the polylinker are lost, a NruI site in the polylinker is created, and the HindII site inside the prepro secretion signal of the α-mating factor 1 becomes unique.

The blunt ended Stu I side was ligated to Eco 47III-digested GlcNAc Tr I in the pUC18 vector. The "prepro-GlcNAc Tr I" coding nucleotide sequence was then isolated from the pUC18 vector through an Eco RI, Hind III double digest. Subsequently, an Eco RI linker was ligated to the blunted Hind III site to allow insertion in the mammalian pCAGGS vector. Directional cloning was carried out with Xba I, Eco RI digested vector and fragment.

Figure 4:
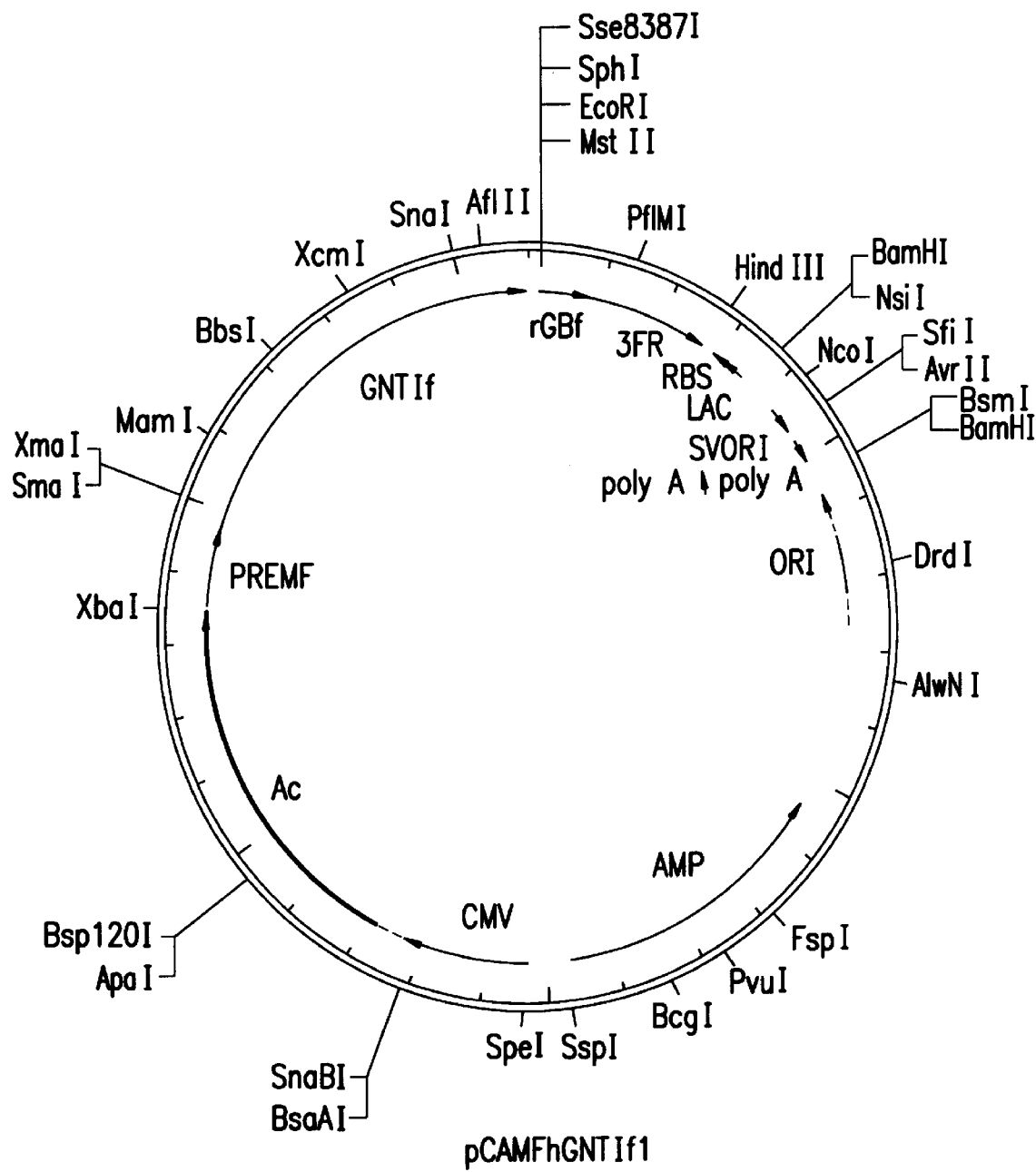
FIG. 4.
Figure 4A:
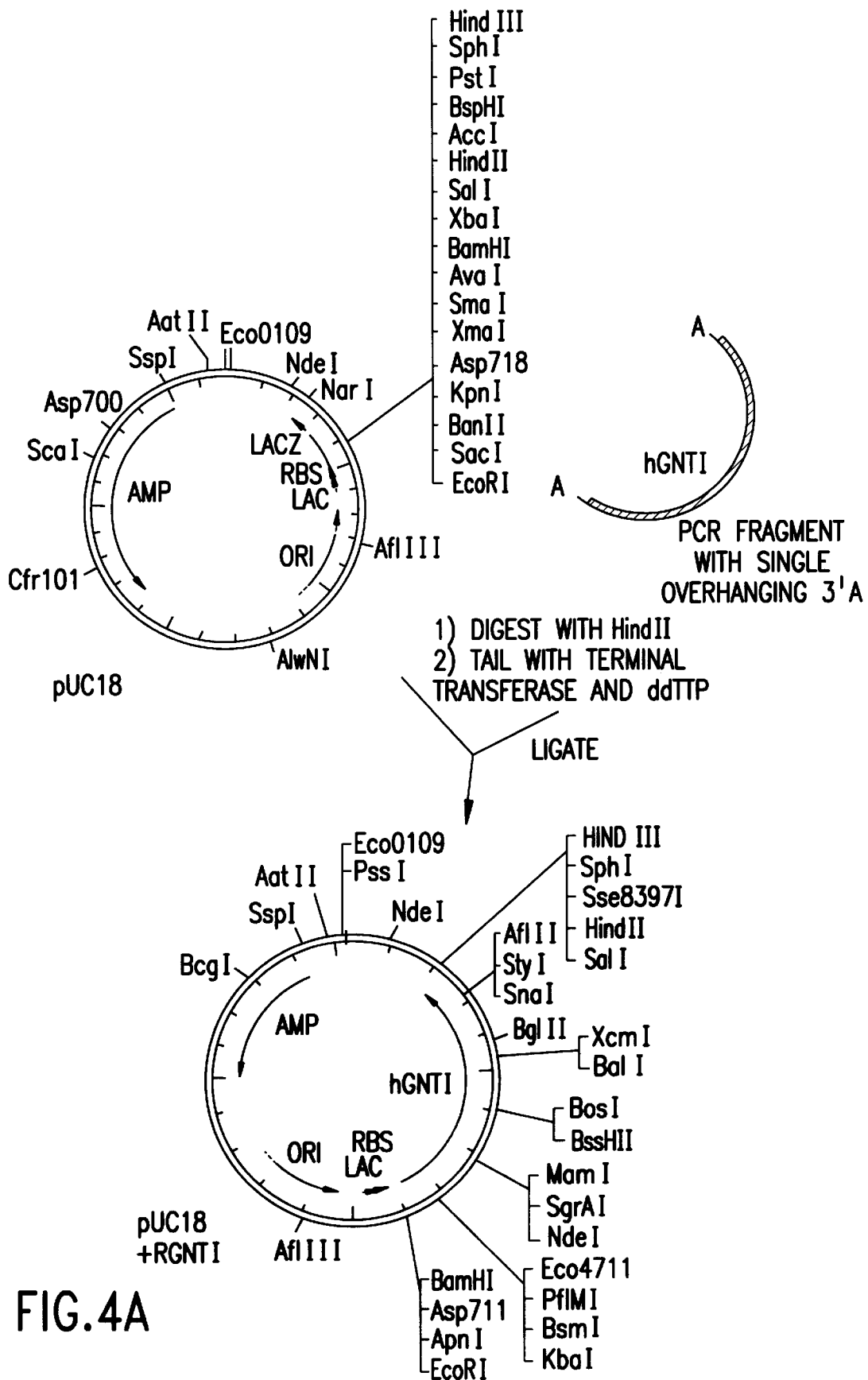
FIGS. 4A, 4B, 4C, 4D and 4E show the sequential construction of pCAMFhGNTIf1. All abbreviations are as above.
Figure 4B:
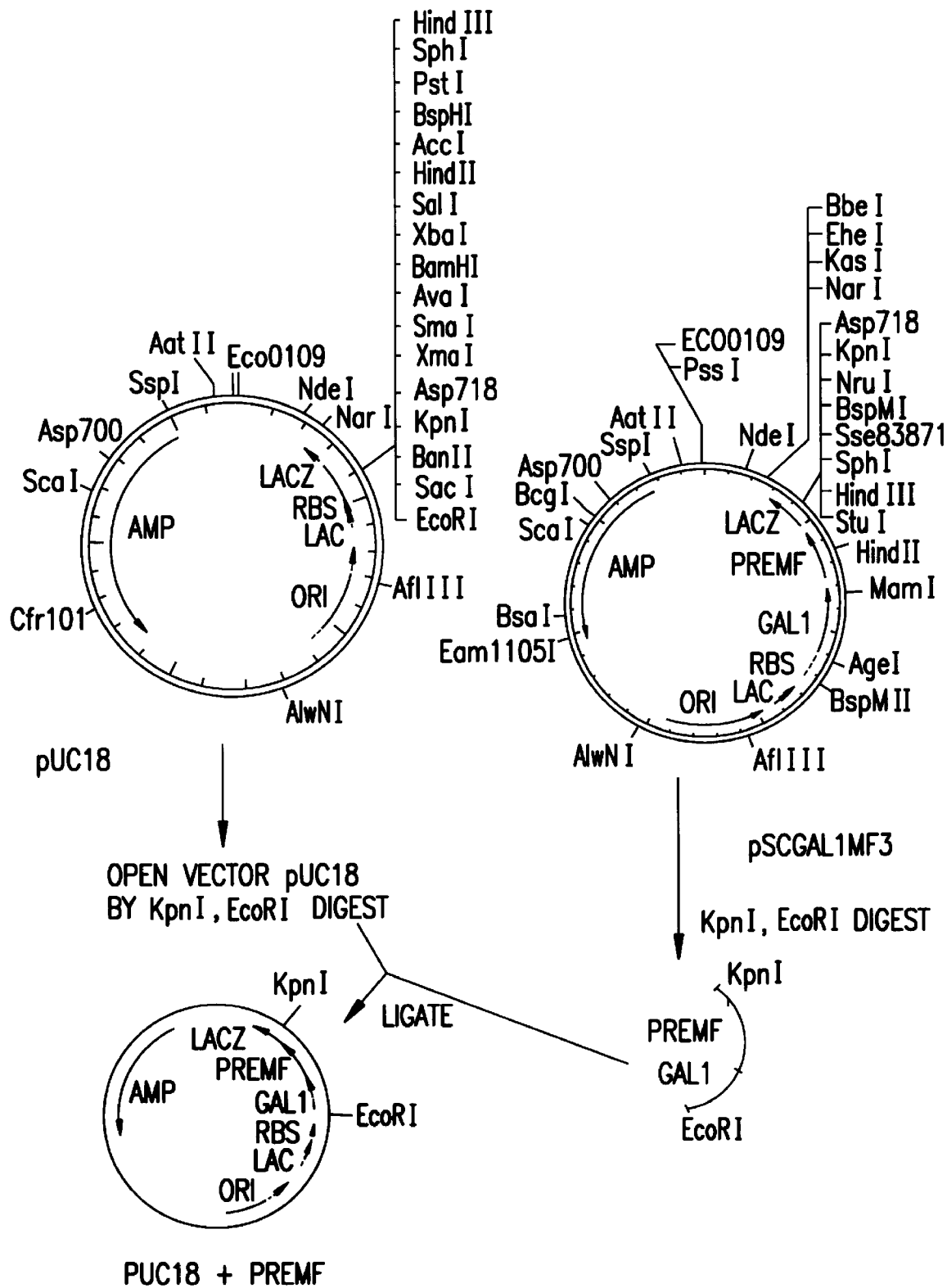
Figure 4C:
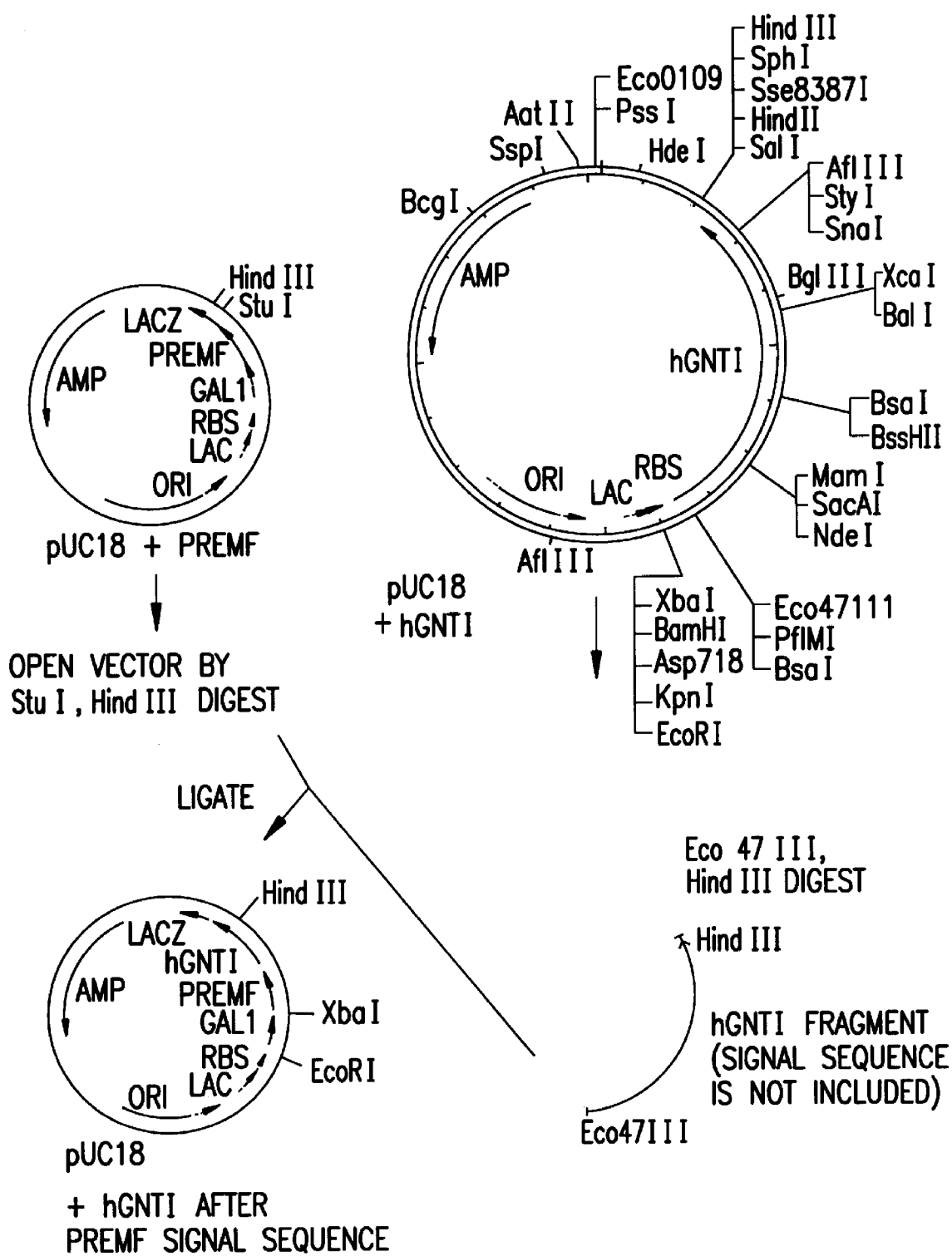
Figure 4D:
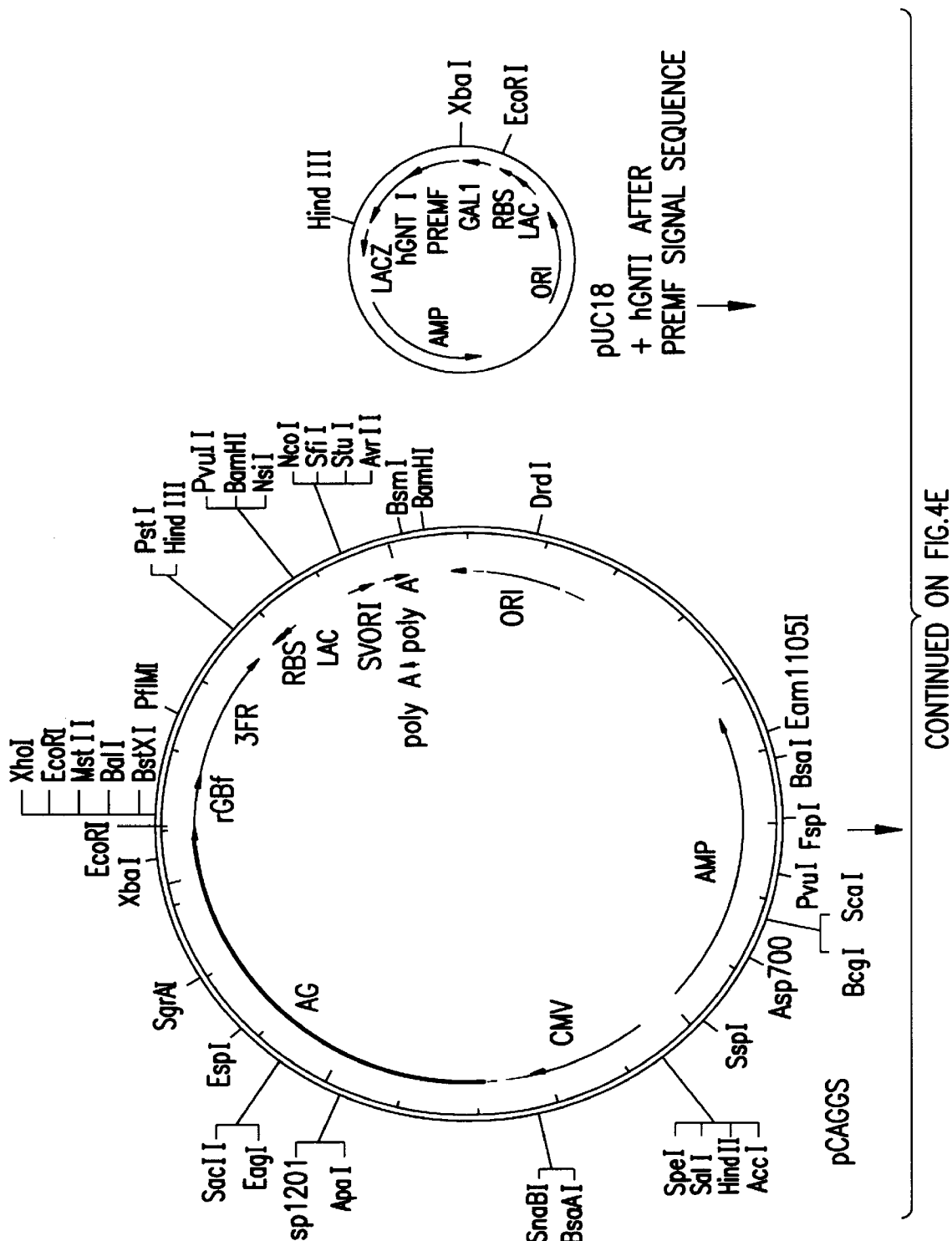
Figure 4E:
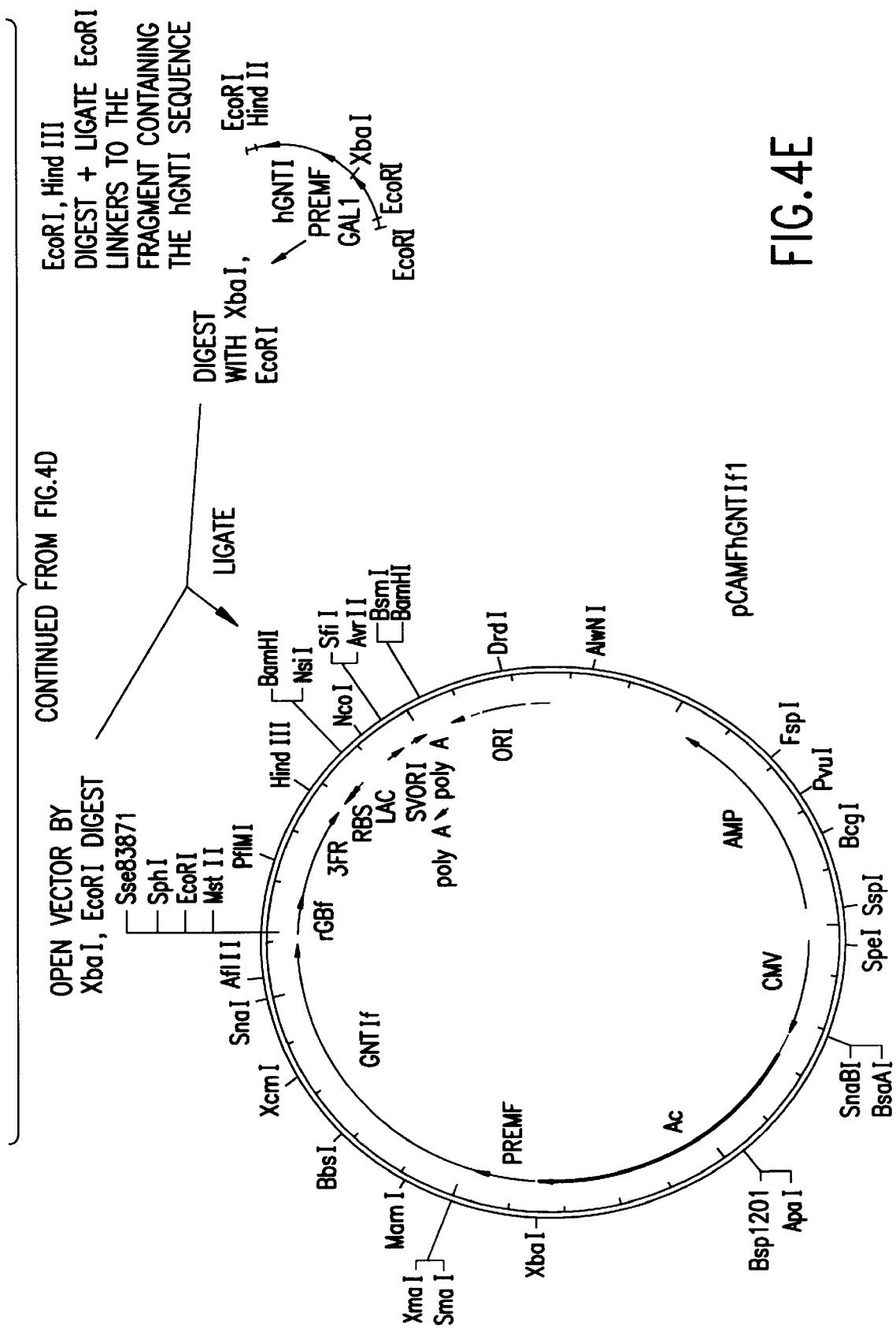

In this expression cassette, the first part of the gene that coded for the secretion and Golgi-retention signals, was replaced by a nucleotide sequence coding for the "prepro" secretion signal sequence of the yeast α-mating factor (Burke et al., *J. Biol. Chem.* 267:24433–24440 (1992); and Brake, A. J., in *Yeast Genetic Engineering* (Barr et al., eds.), Buttersworths Pub., Stoneham, Mass. (1989), pp. 269–280). The vector was called pCAMFhGNTIf1 (FIG. 4). Its construction is diagrammed in FIGS. 4A, 4B, 4C and 4D.

After transient transfection of the vector to COS-7 cells (ATCC CRL-1651), the expressed GlcNAc Tr I enzyme was efficiently secreted in Dulbecco minimal medium (Dulbecco's modified eagle medium, Dulbecco, R. et al., *Virol.* 8:396 (1959); Smith, J. D. et al., *Virol.* 12:185 (1960); Tissue Culture Standards Comm., In Vitro 6:2 and 93 and In Vitro 9:6). The COS supernatant was concentrated about tenfold and was used in GlcNAc Tr I activity assays. GlcNAc Tr I is enzymatically well-characterized and uses a $Man_5GlcNAc_2$ oligosaccharide as a preferred acceptor substrate (Nishikawa et al., *J. Biol. Chem.* 263(17):8270–8281 (1988)). In general, oligosaccharides with the common formula R1α 1,6(Manα 1,3Manβ 1,4GlcNAcR2) are accepted as substrates for GlcNAc Tr I where R1 is one or more mannose residues linked through α bonds; R2 may be β1-4(Fucα1-6)GlcNAc-Asn-X, β1-4GlcNAc-Asn-X, β1-4GlcNAc or H). A GlcNAc residue derived from UDP-GlcNAc was incorporated in the β1-2 linkage to the mannose residue linked α-1,3 to Man β 1,4GlcNAcR2 (Schachter, H., *Glycobiology* 1(5):453–461 (1991)).

Example 5

The GlcNAc Tr I Assay

The mammalian vector pCAGGS and "prepro-GlcNAc Tr I" coding sequences (pCAMFhGNTIf1) were transfected into COS cells according to the protocol of McCutchan et al. (*J. Nat. Cancer Inst*. 41:351–357 (1968)). GlcNAc Tr I was secreted in Dulbecco minimal medium without serum. The enzyme was concentrated by ultrafiltration in Centricon-30™ centrifugal microconcentraters (Amicon).

GlcNAc Tr I activity was assayed according to a method described by Nishikawa et al. (*J. Biol. Chem*. 263(17) :8270–8281 (1988)) as follows. In a total volume of 0.030 ml, the following were added: 0.33 mM $Man_5Gn$; 0.1M 2-[N-morpholino]ethanesulfonic acid (MES) (pH 6.1); 20 mM $MnCl_2$; 5 mM AMP (as pyrophosphatase inhibitor); 0.1M GlcNAc (as β-N-acetylhexose-aminidase inhibitor); 0.34 mmol UDP-($^{14}$C)GlcNAc (Amersham); and 10 μl concentrated COS supernatant. Incubation was at 37° C. for 1 to 4 hours. The proteins were then separated from the oligosaccharides through precipitation by the addition of 100% ice-cold ethanol to a final concentration of 66%.

Oligosaccharides were separated on silica 60 high-performance thin-layer plates using a solvent containing butanol/acetic acid/water (20:10:10; v/v/v). The plates were developed twice in the same solvent (Vauhkonen et al., *Eur. J. Biochem*. 152:43–50 (1985)). Radioactive oligosaccharides were visualized after exposure of the TLC plate to an X-ray film for several days.

Oligosaccharides were also visualized by orcinol staining as follows. A mixture of 0.6% orcinol in 10% sulfuric acid and 0.1% $Fe(III)Cl_2$ was sprayed on top of the TLC plate which was subsequently heated to 100° C. for 10 to 15 minutes.

Instead of oligosaccharides, where noted, glycoproteins were added to the reaction mixture for GlcNAc Tr I. About 10 μg glycoprotein (e.g. ovalbumin) was added to the 30 μl reaction mixture. Incubation at 37° C. was over a period of 6 to 18 hours. The incorporation of radioactive GlcNAc into the oligosaccharide units on the proteins, separated on a SDS-polyacrylamide gel (Laemmli, U. K., *Nature* 227:680–685 (1970)), was visualized by autoradiography.

Example 6

Galactosyltransferase and Sialyltransferase Processing

Additional in vitro modifications of N-acetylglucosamine-bearing glycoproteins or oligosaccharides were carried out with β-1,4 galactosyl transferase from human milk and α-2,6 sialyltransferase from rat liver. Both enzymes were obtained from Boehringer Mannheim.

Before carrying out these processing steps, CBH I was purified from the GlcNAc Tr I reaction mixture. A description for the purification of this protein is available from Shoemaker et al., *Bio/Technology* 1:687–690 (1993). Briefly, the COS cell medium was passed over a DEAE-sepharose column that had been equilibrated in 50 mM sodium-acetate buffer, pH 5. Cellulases (or CBH I alone) from *T. reesei* in a reaction mixture for GlcNAc Tr I treatment, were dialyzed to 50 mM sodium acetate buffer, pH 5. Then, they were separated from COS supernatant proteins through purification on a DEAE Sepharose® column (volume: 0.5 ml, about 1 cm in height, 0.5 cm diameter, fast flow resin, Pharmacia). Under these conditions, CBH I was retained.

A salt gradient (changing the NaCl concentration from 0-to 0.1M in 400 μl sodium acetate buffer, pH 5) removed a substantial part of the proteins present in the reaction mixture for the in vitro glycosylations, and CBH I was retained on the column. The salt concentration was further raised to 0.2M (in 800 μl), and CBH I eluted at 0.15M NaCl or higher. The salt concentration was further raised to 0.5M (by applying 800 μl) in order to elute as much of the CBH I from the column as possible. The CBH I-containing fractions were pooled and were dialyzed against a 50 mM Tris buffer, pH 8, and concentrated about 10-fold, using a Centricon ultracentrifugation device (Amicon). CBH I was then added to the reaction mixture for galactosyltransferase: β-1,4 galactosyl transferase required a pH of 8–8.5 and the presence of manganese for optimal specific activity (Schanbacher et al., *J. Biol. Chem*. 245:5057–5061 (1970); Yoon et al., *Glycobiology* 2:161–168 (1992)). To the GlcNAc Tr I-treated proteins or oligosaccharides were added: 0.17 μmol UDP ($^{14}$C)Gal (285 mCi/mmol) or "cold" UDP-Gal; 2 milliunits galactosyltransferase; and $MnCl_2$ to a final concentration of 20 mM in a final volume of 0.030 ml. Galactosylation was carried out at 37° C. for about 8 hours.

α-2,6 Sialyltransferase required a pH of 6–6.5 for optimal activity (Weinstein et al., *J. Biol. Chem*. 257:13845–13853 (1982)). To the galactosyltransferase-reaction mixture, the following were added: 0.18 μmol CMP ($^{14}$C)NANA (281 mCi/mmol) (Amersham) to a final concentration of 6 mM; 2 milliunits α-2,6 sialyltransferase; and NaCl (to stabilize the sialyltransferase, final concentration: 50 mM). The pH was adjusted to 6–6.5 through the addition of 1M MES. The final volume of the reaction mixture was 0.050 ml. The reaction mixture was incubated at 37° C. for 8 hours. The incorporation of radioactive sugar-residues on glycoproteins was visualized as described above.

Example 7

Improvement of Hybrid Glycoprotein Structures with α-1, 2 Mannosidase

Glycoproteins (up to 100 mg) or oligosaccharides (prepared from about 100 mg of protein) were treated with 2 to 6 μunits *A. saitoi* α-1,2 mannosidase (Oxford Glycosystems) in 100 mM sodium-acetate (pH 5) for 18 hours at 37° C. Glycoproteins were dialyzed to 20 mM MES, pH 6.1, before further processing with GlcNAc Tr I. Incorporation of radioactive GlcNAc on oligosaccharides was visualized on X-ray film after separation through TLC. Radioactive signals originating from ($^{14}$C)GlcNAc-residues on proteins were visualized as described above.

Example 8

Mannosidase and Mannosyltransferase Assays

Mannosidase activity was assayed in the extracellular medium from *T. reesei* and *Aspergillus satoi*: *T. reesei* RUTC 30 was grown in minimal medium, according to Uusitalo et al. (1991) with 2% lactose as a carbon source. The same medium, supplemented with 2% glucose was used in parallel in order to determine whether there is an influence of different carbon sources on expression of mannosidases. *Aspergillus saitoi* was grown on minimal medium according to Czapek (Onions and Pitt, Appendix: Media. In Hawksworth, D. L. and Kirsop, B. E., (Eds.), Living resources for biotechnology. Cambridge University Press, Cambridge, UK, pp. 180–199, (1988) with 1% yeast extract and, in parallel 2% glucose as the carbon sources. After 4 days fermentation at 28° C., fungal cells were separated from growth medium by filtration over a GF/F glass microfiber filter (Whatman).

The growth medium was further concentrated (70 fold), using centriprep and centricon ultracentrifugation devices (M.W. cut off: 10 kD; Amicon). Reaction mixtures for assaying mannosidase activities contained in a volume of 20 µl: 500 ng ANTS labelled high mannose oligosaccharides from ribonuclease B (Oxford Glycosystems); Sodium cacodylate pH 6.1 (60 mM final concentration); CaCl2 (20 mM) and 15 µl concentrated growth medium. Incubation of the reaction mixtures was overnight at 37° C. Oligosaccharides were then separated on a polyacrylamide gel as described.

The collected fungal cells were used for preparation of crude extracts: after washing with 50 mM sodium cacodylate buffer, the dry cell pellet was ground in a mortar using liquid nitrogen. Broken cells were transferred to ice cold sodium cacodylate buffer (50 mM, pH 6.1) containing MgCl2 (15 mM) and a cocktail of protease inhibitors (PMSF, leupeptin, benzamidin, aprotinin in concentrations prescribed by the manufacturer (Boehringer Mannheim). Cells were left in buffer on ice for 30 minutes. We used differential centrifugation to obtain 15000 g, 40000 g and 100000 g membrane pellets. Finally Triton X 100 (2% final concentration) was added to solubilize enzymes from the membranes. Reaction mixtures for assaying mannosidases were prepared as already described. Reaction mixtures for assaying mannosyltransferases contained in a volume of 20 µl: 100 ng ANTS labelled Man$_8$GlucNAc; 10 µg UDP-mannose; MnCl$_2$ (20 mM final concentration) and 10 µl of the 100000 g membrane preparation. The reaction mixtures were incubated for 4 hours at 37° C.

Example 9

Glycoproteins as Acceptor Substrates for GlcNAc Tr I

Different glycoproteins were used in GlcNAc Tr I activity assays to determine whether they were carrying glycosyl structures that were substrates for GlcNAc Tr I. Ovalbumin, which was used as a positive control in this experiment, has two candidate glycosylation sites, but only one site is actually glycosylated. A fraction of the oligosaccharides that are present on ovalbumin is Man$_5$Gn$_2$ (Tai et al., *J. Biol. Chem.* 252:6687–6694 (1977)). As negative controls, *S. cerevisiae* invertase and human transferrin were used. Invertase from *S. cerevisiae* carries high mannose oligosaccharides with Man$_8$Gn$_2$ being the smallest structure formed (Trimble et al., *J. Biol. Chem.* 261:9815–9824 (1986)). Transferrin, a human glycoprotein, has two complex-type N-glycans (März et al., *Can. J. Biochem.* 60:624–630 (1982)). Most transferrin oligosaccharides are bi-antennar with sialic acid as terminal sugar-residues.

Figure 5:
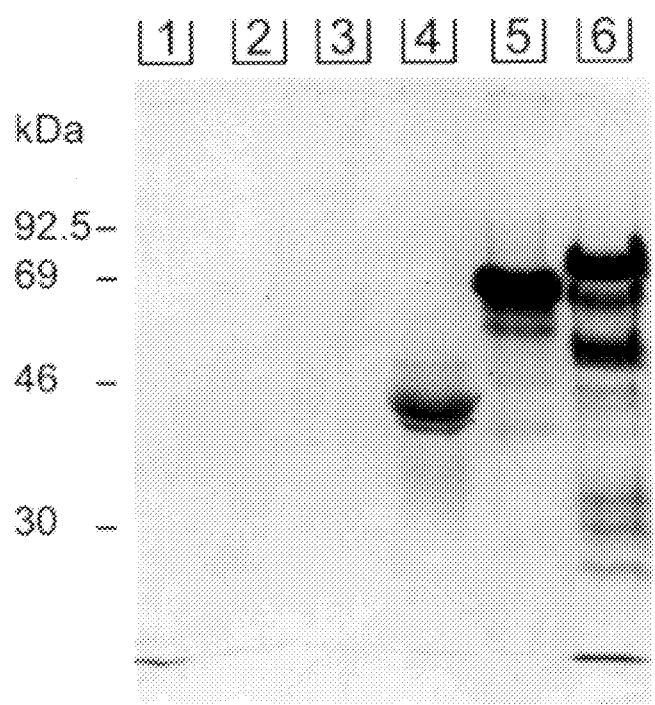
FIG. 5.

Proteins secreted from the *T. reesei* mutant strain RUTC 30 and cellulases from an unknown strain of *T. reesei* (commercial source; Fluka, Buchs, Switzerland) were studied. *T. reesei* mutant strain RUTC 30 has an increased capacity to secrete proteins (Ghosh et al., in *Trichoderma reesei Cellulases: Biochemistry, Genetics, Physiology & Application* (Kubicek et al., eds.), Royal Soc. of Chemistry, Cambridge, England (1990), pp. 115–138). The results (FIG. 5) show that radioactive ($^{14}$C)GlcNAc was transferred from UDP-($^{14}$C)GlcNAc to oligosaccharides on ovalbumin and on extracellular secreted proteins from both *T. reesei* strains. These results indicated the presence of trimming enzymes in *T. reesei* which were capable of the in vivo formation of acceptor-oligosaccharides for GlcNAc Tr I.

Example 10

Free Oligosaccharides as Acceptor Substrate for GlcNAc Tr I

Figure 6:
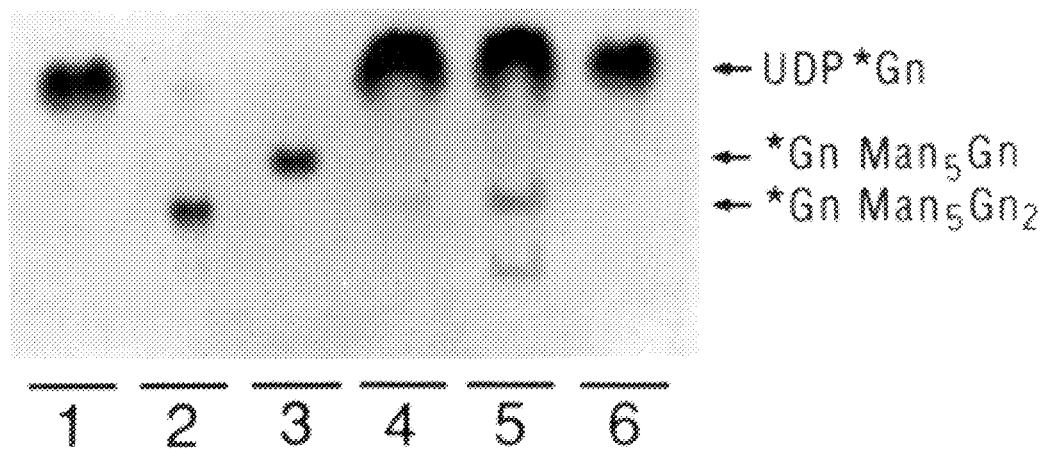
FIG. 6.

The oligosaccharides from Trichoderma extracellular glycoproteins were isolated to further evaluate and confirm that Man$_5$GlcNAc$_2$ was the GlcNAc accepting N-glycan. Oligosaccharides were enzymatically removed with N-glycanase. This enzyme releases all types of N-linked sugar chains through cleavage of the glycosylamine linkage to asparagine residues (Tarentino et al., *Biochemistry* 24:4665–4671 (1985)). The oligosaccharides were then tested in a reaction mixture containing GlcNAc Tr I. A commercial mixture of oligosaccharides ranging from Man$_9$GlcNAc$_2$ to Man$_5$GlcNAc$_2$ obtained from ribonuclease B through hydrazinolysis (Oxford GlycoSystems No. RP-2500) were used as a positive control for this experiment (Liang et al., *J. Biochem.* 88:51–58 (1980)). Oligosaccharides that had been enzymatically released from *S. cerevisiae* invertase were used as negative controls. GlcNAc Tr I transferred radioactive GlcNAc from UDP-($^{14}$C)GlcNAc to fungal Man$_5$GlcNAc$_2$ glycans. This was detected after separation of the manipulated oligosaccharides through thin layer chromatography (TLC). The position of the labelled fungal oligosaccharides, as revealed by autoradiography (FIG. 6), coincided with that of the positive control. With the *T. reesei* mutant strain RUTC 30 an additional oligosaccharide structure that was larger than Man$_5$GlcNAc$_2$ also acted as an acceptor for GlcNAc Tr I. This indicated the existence of differences in glycosylation patterns at the strain level.

Example 11

Galactosyltransferase and Sialyltransferase Assays

Additional in vitro modifications of GlcNAc-bearing glycoproteins or oligosaccharides were carried out with the commercial β-1,4 galactosyl transferase (Boehringer Mannheim) from human milk (Schanbacher et al., *J. Biol. Chem.* 245:5057–5061 (1970)) and commercial α-2,6 sialyltransferase (Boehringer Mannheim) from rat liver (Weinstein et al., *J. Biol. Chem.* 257:13845–13853 (1982)). Galactosylation was demonstrated through the incorporation of radioactive galactose on in vitro synthesized, non-labelled, GlcNAc-bearing glycosylstructures. The completion of the synthetic pathway was demonstrated through the incorporation of radioactive sialic acid on "cold" galactose that was added in a β-1,4 linkage to GlcNAc. Glycoproteins labelled in this manner were separated through electrophoresis on a SDS-polyacrylamide gel. During electrophoresis, sialylated glycoproteins moved slower compared to non-sialylated proteins. This was observed as a shift of the sialylated proteins towards higher molecular weights. To clearly demonstrate this effect, one Trichoderma protein, namely cellobiohydrolase I (CBH I), was examined in particular.

After the GlcNAc Tr I processing step, CBH I was purified from the COS supernatant-containing reaction mixture by ion-exchange chromatography on DEAE Sepharose (Shoemaker et al., *Bio/Technology* 1:687–690 (1983)). The purification step avoided any potential interference by COS supernatant proteins, which also can be an acceptor for sialyltransferase.

Figure 7:
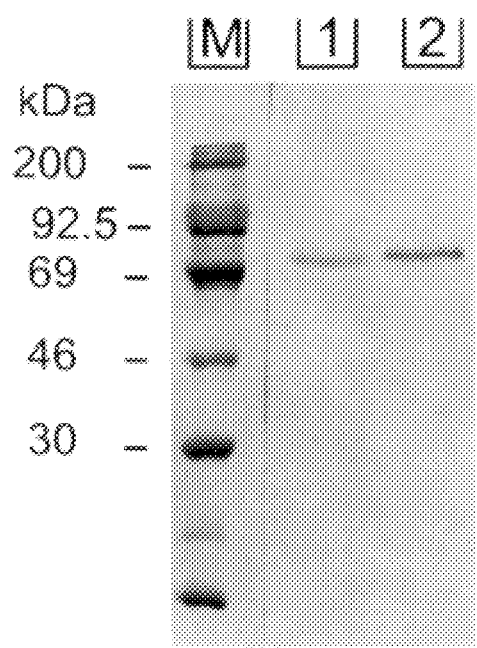
FIG. 7.

An autoradiogram was obtained with CBH I-containing radioactive GlcNAc versus radioactive sialylated CBH I (FIG. 7). A clean shift in the electrophoretic mobility of the sialylated CBH I as compared to the GlcNAc-containing form was shown. This demonstrated that it was possible to modify the naturally occurring glycosylstructures on Trichoderma CBH I into hybrid structures with terminal sialic acid residues. The two final modification steps were confirmed on the free oligosaccharides. The incorporation of galactose followed by the incorporation of sialic acid, always caused a shift in the molecular weight of the oligosaccharide molecules. This was observed as shifts in the mobility of the differently manipulated oligosaccharides in TLC.

Example 12

Improvement of Hybrid Glycoprotein Structure Through the Use of α-1,2 Mannosidase When using a fungus such as *T. reesei* to produce heterologous, therapeutically valuable proteins, a substantial fraction of the high mannose oligosaccharides will not be an acceptor for GlcNAc Tr I. On the other hand, in mammalian cells, an α-1,2 mannosidase that is present in the cis-compartment of the Golgi apparatus trims most, if not all, high mannose structures to $Man_5GlcNAc_2$ and thus assures that carbohydrate chains are convertible to the complex type (Tulsiani et al., *J. Biol. Chem.* 263:5408–5417 (1988)).

A commercial α-1,2 mannosidase (Oxford Glycosystems, Oxford, UK) from *A. saitoi* (Yamashita et al., *Biochem. Biophys. Res. Comm.* 96:1335–1342 (1980)) was used to investigate to what extent glycosylation processing resembled that of mammalian cells. The effect of preincubation of fungal oligosaccharides or glycoproteins with α-1,2 mannosidase on the in vitro incorporation of GlcNAc in a GlcNAc Tr I assay was determined.

Figure 8:
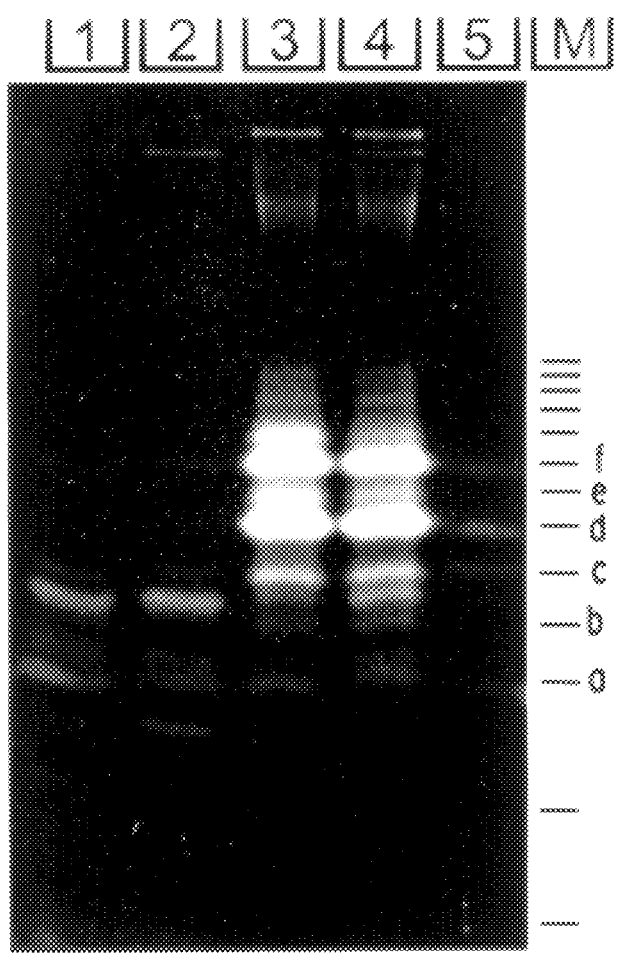
FIG. 8.

Oligosaccharides from bovine ribonuclease B, from *T. reesei* extracellular proteins were treated with *A. saitoi* α-1,2 mannosidase. Treated and non-treated N-glycans were processed and visualized by fluorophore labelling of reducing saccharides (FIG. 8). In this method, the reducing end of saccharides, liberated as described above, was reacted with 8-aminonaphthalene-1,3,6-trisulfonic acid (ANTS), as described by Jackson, P., "Methods in Enzymology. Guide to techniques in Glycobiology", Vol. 230, p. 250–265, Eds. Lennartz, W. & Hart, G. (1994)). Basically, 10 µl of 0.15M ANTS in acetic acid-water solution (3:17 v/v) and 10 tl of 1M sodium cyanoborohydride, dissolved in DMSO were added to lyophilized oligosaccharides, enzymatically released from 400 µg glycoprotein or to 5 µg of bovine ribonuclease B oligosaccharides, commercially obtained from Oxford Glycosystems. No prior purification of oligosaccharides on a Biogel P2 column was necessary. After overnight incubation at 37° C., ANTS labelled oligosaccharides were precipitated through addition of 4 volumes of ice cold acetone (at minus 20° C). The oligosaccharides were pelleted through centrifugation (for 4 minutes at 10,000×g). Unreacted ANTS in the acetone containing supernatant was removed. Oligosaccharides were redissolved in a suitable volume of glycerol:water (1:4 v/v) and stored at minus 70° C. ANTS derivatized oligosaccharides were separated on a 30% acrylamide, 0.8% N,N'-methylene-bisacrylamide gel (on the SE 250 Mighty Small II electrophoretic apparatus, that is also used for separation of proteins through PAGE). In order to obtain "crystal clear" gels, the gel solution was poured between plastic sheets that were adhered to the mold plates with water. Stacking of the oligosaccharides was allowed at a current of 15 mA for 30 minutes, while separation happened at a current of 30 mA for 2.5 hours. As a reference standard, a glucose ladder was loaded, obtained after digestion of wheat starch (described by Jackson, P., "Methods in Enzymology. Guide to techniques in Glycobiology", Vol. 230, p. 250–265, Eds. Lennartz, W. & Hart, G. (1994)). The electrophoretic band patterns were viewed on a UV transilluminator and photographed through a red filter (Cokin A. 003; Cromofilter SA, Paris, France), using standard black-and-white film. A polaroid type 667 film with a speed of ISO3000 and an aperture of 4.5 required an 8 sec exposure (FIG. 8).

The oligomannose-type N-glycans from ribonuclease B, ranging from $Man_5GlcNAc_2$ to $Man_9GlcNAc_2$, were all converted to $Man_5GlcNAc_2$. This agreed with the fact that the biosynthesis of N-linked sugar chains on ribonuclease B is known to be arrested at an intermediary stage of processing, as demonstrated by the fact that high mannose structures had not all been converted to $Man_5GlcNAc_2$ and had extra mannose residues only in the α-1,2 linkage. Oligosaccharides which had been isolated from a mixture of proteins secreted from *T. reesei* were partly converted to $Man_5GlcNAc_2$, whereas a substantial part of the oligosaccharide pool was not converted. From the starting material, a fraction of the oligosaccharides seemed to be smaller than $Man_8GlcNAc_2$, while another fraction was larger than $Man_9GlcNAc_2$. In FIG. 8, only trimming of *T. reesei* oligosaccharides is shown.

Figure 9:
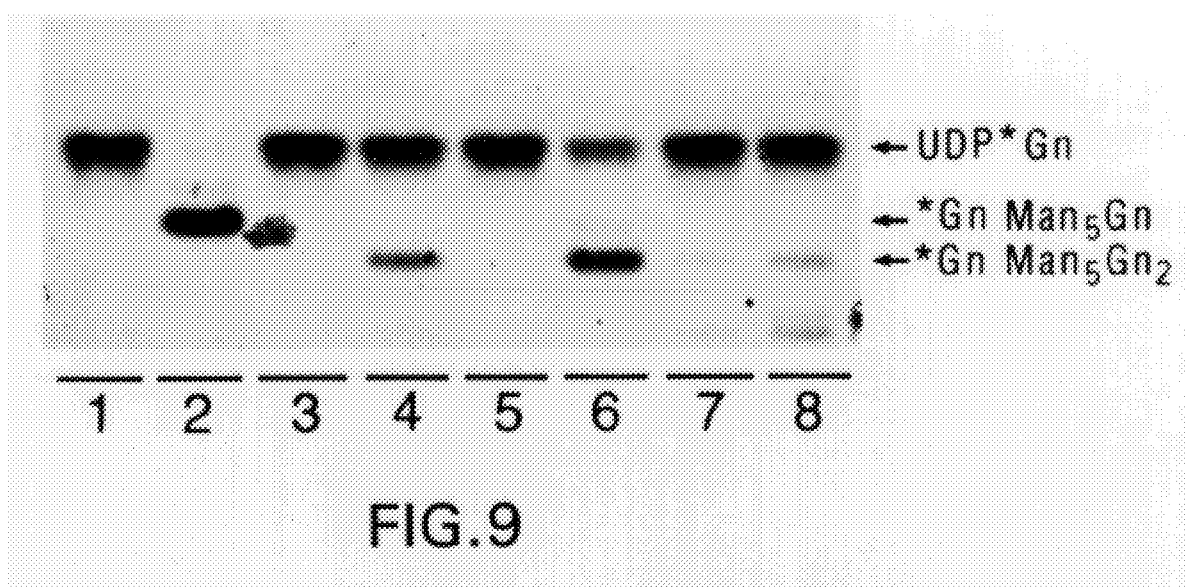
FIG. 9.

The fungal oligosaccharides that had been treated with *A. saitoi* α-1,2 mannosidase were then added to a reaction mixture for GlcNAc Tr I. The oligosaccharides were analyzed by thin layer chromatography. α-1,2 Mannosidase treatment in vitro favored the formation of acceptor substrate for GlcNAc Tr I (FIG. 9) because much more radioactive GlcNAc was incorporated into the fungal oligosaccharides. A small fraction of the *S. cerevisiae* invertase oligosaccharides was also trimmed to the GlcNAc-accepting high mannose structure. $Man_5GlcNAc_2$ glycans isolated from ovalbumin were the positive control for this experiment. On the autoradiogram, the position of the labelled fungal oligosaccharides coincided with that of the positive control. This confirmed the formation of GlcNAcMan5GlcNAc2 in the different reaction mixtures.

Figure 10:
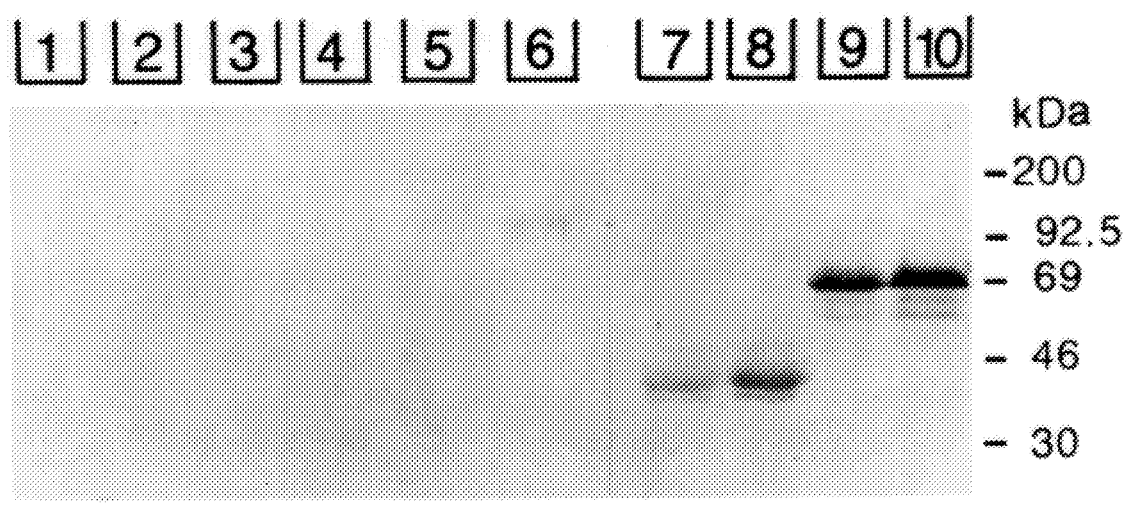
FIG. 10.

With the RUTC 30 Trichoderma strain, α-1,2 mannosidase treatment also gave rise to more of a second, larger GlcNAc-accepting oligosaccharide. When the mannosidase treatment was repeated on intact glycoproteins (FIG. 10) the results were analogous with those obtained with free oligosaccharides. That is, more labelled GlcNAc was transferred to ovalbumin and to *T. reesei* glycoproteins when they were first pretreated with α-1,2 mannosidase. GlcNAc now was also transferred to *S. cerevisiae* invertase.

In summary, the method of the invention allows the production of mammalian-like, hybrid oligosaccharides on glycoproteins secreted from the filamentous fungus *T. reesei* and its mutant strain *T. reesei* RUTC 30. The in vitro experiments used the following mammalian glycosyltransferases: human GlcNAc Tr I produced in COS cells; β-1,4 galactosyl transferase from human milk and α-2,6 sialyltransferase from rat liver. Preincubation with α-1,2 mannosidase from *A. saitoi* substantially improved GlcNAc incorporation into the fungal proteins. This embodiment obtained a fungus that synthesized oligosaccharides that were convertible to complex mammalian-type structures in the simplest possible way. Since the first steps of the complex carbohydrate synthetic pathway were executed in vivo in a fungus such as Trichoderma, completion of the glycosylation pathway was possible through in vitro enzymatic oligosaccharide synthesis and modification. As a result of this invention, large scale stereo-controlled oligosaccharide synthesis will be possible in the future (Ichikawa et al., *Anal. Biochem.* 202:215–238 (1992)). The fact that a fungus can be manipulated to construct well-defined and uniform glycosyl structures on its secreted proteins offers possibilities to investigate the biological significance of oligosaccharide diversity and to perform carbohydrate engineering. For certain proteins, the production of a single glycoform may be produced to obtain a uniform therapeutic profile (Stanley, P., *Molecular and Cellular Biology* 9:377–383 (1989)).

Example 13

Analysis of the N-glycan Profile of *T. reesei* Glycoproteins by Fluorophore Labelling A detailed image, both quantitatively and qualitatively, was obtained when oligosaccharides were derivatized with the fluorophore 8-aminonapthalene-1,3,6 trisulphonate and subsequently electrophoretically separated on a polyacrylamide gel. In FIG. 4, we demonstrate the oligosaccharide pattern from *T. reesei* RUTC 30 cellobiohydrolase I, purified after fermentation in minimal medium (Nyyssönen et al., *Bio/Technology* 11:591–595 (1993)). The pattern obtained with a mixture of proteins secreted by the same Trichoderma strain, but in a different growth medium (according to Uusitalo et al., 1991) is also shown. Only a minor fraction of oligosaccharides from the starting material seems to be $Man_5GlucNAC_2$. More abundant are $Man_6GlucNAC_2$, $Man_7GlucNAC_2$, $Man_8GlucNAC_2$ and $Man_9GlucNAC_2$ oligosaccharides. N-glycans larger than $Man_9GlucNAC_2$ were also found.

With pure CBH I, oligosaccharides even smaller than $Man_5GlucNAC_2$ were isolated. In general, the Trichoderma sugar chains are clearly much smaller than those isolated from *Saccharomyces cerevisiae* glycoproteins. Since α-1,2 mannosidase trimming is incomplete (FIG. 8), it is very likely that mannose residues are present in linkages different from the α-1,2 linkage due to transfer to trimming products by one or more mannosyl transferases.

Example 14

Determination of *T. reesei* Mannosidase and Mannosyltransferase Activities and Conclusions In order to investigate further in detail the resemblance between *T. reesei* glycosyl synthesis and the mammalian system, we tried to localize the mannosidase activity responsible for the oligosaccharide panel on the secreted fungal proteins. First, we checked whether mannosidases were present in the extracellular medium of the fungus, which could eventually be responsible for "postsecretional" trimming of the oligosaccharides on other secreted proteins. We developed an assay to determine this activity as follows: oligosaccharides from bovine ribonuclease B (commercially available as a reference panel from Oxford Glycosystems) were used as substrate for mannosidases. A complete conversion to $Man_5GlucNAC_2$ is obtained if enough α-1,2 mannosidase is present. $Man_5GlucNAC_2$ is further trimmed if α-1,3 and/or α-1,6 mannosidases are present. After labelling with ANTS, the ribonuclease B reference oligosaccharides were added to 70 fold concentrated extracellular medium from a four day old *T. reesei* culture (with fungal cells removed). A four day old, concentrated culture supernatant from *Aspergillus saitoi* was used as a positive control for this assay: it is known that the latter organism secretes different mannosidases (an α-1,2 and α-1,3(6) mannosidase) when grown on minimal medium containing mannan as the carbon source (Keskar, S.S. et al., *Biotechnology Letters* 15:695–690 (1993)). In FIG. 7, we demonstrate the result of an overnight incubation of the reaction mixtures: the α-1,2 mannosidase activity from *A. saitoi* is clearly detectable. Most ribonuclease B oligosaccharides are trimmed to $Man_5GlucNAC_2$. No or only marginal quantities of mannosidase are present in the medium of *T. reesei*, since the ribonuclease reference panel remained untouched. We mention here that *T. reesei* secreted many more proteins in its minimal medium (about 300 µg/ml) than did *A. saitoi* (barely detectable, using the Bradford assay).

Using the same ANTS labelled oligosaccharide panel from ribonuclease B, we found intracellular mannosidase activity in crude extracts from *T. reesei*, *A. saitoi*, L929 mouse cells and from *S. cerevisiae*. We further tried to discriminate mainly between mannosidases, active in glycosylation processing in the endoplasmic reticulum, the Golgi apparatus and those active in vacuoles. Using differential centrifugation or sucrose gradients to separate organelles, prepared from *T. reesei* cells, we did not obtain sufficient resolution of different mannosidase activities in different organelles. However, α-1,2 mannosidase activity was abundantly present in fractions that were enriched for mannosyltransferase activity. Determination of the mannosyltransferase activity was done after adaptation of the assay, described by Nakajima and Ballou (*Proc. Natl. Acad. Sci. USA* 72:3912–3916 (1975)). With reaction mixtures containing UDP-mannose as sugar-donor, ANTS labelled $Man_8GlucNAC$ as a substrate and glycosylation enzymes solubilized from the membrane preparations by Triton X 100, mannosyltransferase activity was demonstrated by retardation in the electrophoretic mobility of the substrate oligosaccharides (results not shown).

The examples above demonstrate that it is possible to construct mammalian-like, hybrid oligosaccharides on glycoproteins secreted from the filamentous fungus *Trichodertna reesei*. Mammalian glycosyltransferases, namely human N-acetylglucosaminyl transferase I produced in COS cells, β-1,4 galactosyl transferase from human milk, and α-2,6 sialyltransferase from rat liver, were used to mimic in vitro the glycosylation synthesis pathway as it occurs in mammalian cells. Preincubation with α-1,2 mannosidase from *Aspergillus saitoi* substantially improved GlucNAc incorporation on the fungal proteins. With free N-glycans isolated from *Trichoderma reesei* cellulases, it was demonstrated that not all sugar chains are convertible to the ideal acceptor substrate for GlucNAc Tr I: $Man_5GlucNAC_2$. The majority of the N-linked oligosaccharides resemble the high mannose structures present on certain proteins from mammalian cells, ranging predominantly from $Man_5GlucNAC_2$ to $Man_9GlucNAC_2$. With pure CBH I, obtained after fermentation in Trichodenna minimal medium (Nyyssönen et al., 1993) a substantial fraction of the oligosaccharides seems to be even smaller than $Man_5GlucNAC_2$. Using another fermentation medium, we now also obtained oligosaccharides larger than $Man_9GlucNAC_2$. The electrophoretic mobility of CBH I produced in the different media also changed notably. After deglycosylation, CBH I produced as described by Nyyssönen et al., (1993) shifted only slightly compared to the original form after electrophoretic separation on a polyacrylamide gel. Exhaustive digestion (long incubation time and many units N-glycanase) was needed to liberate oligosaccharides. With the growth conditions we used, CBH I was easily deglycosylated, giving rise to a pronounced electrophoretic shift compared to the original protein (results not shown). The effects, environmental factors can have on protein glycosylation are profoundly described by Goochee and Monica (*Bio/Technology* 8:421–427 (1990), *Bio/Technology* 9:1347–1355 (1991)). Their reviews strengthen our belief that the growth medium can be the cause of the differences in glycosyl patterns found on Trichoderma proteins.

From the experiments we conducted to elucidate the localization of the mannosidase(s) responsible for the small N-glycans on Trichoderma secreted proteins. The possibility of secretion of mannosidases that could act on the other secreted fungal proteins seems very unlikely. Even with very concentrated growth medium and after a long incubation time, no trimming at all of substrate oligosaccharides occurred.

We presume that processing in the Trichoderma Golgi apparatus resembles partly that of mammalian cells and partly that of yeast: Mannosidases capable of trimming back the Trichoderma N-glycans to $Man_5GlucNAC_2$ seem to be present. On the other hand, mannosyltransferases capable of transferring mannose residues in linkages different from the α-1,2 linkage, are also present. The latter conclusion was confirmed after carrying out mannosyltransferase assays, analogous to the one described by Nakajima and Ballou (1973): using ANTS labelled $Man_8GlucNAc$ as a substrate, we managed to demonstrate incorporation of up to two mannose residues. On the other hand, $Man_5GlucNAc$ was no substrate for mannosyl transferases. Hence, we wonder if $Man_5GlucNAC_2$, the crucial structure for synthesis of complex sugar structures, will not be a substrate for mannosyl transferase(s) "in vivo" in *T. reesei*.

It is not yet known how similar glycosylation synthesis in *Trichoderma reesei* proceeds to that in mammalian cells. Therefore it is difficult to evaluate whether this organism can be easily manipulated to have more, if not all, of the glycosyl groups converted to mammalian-like structures. The in vitro experiments are an introductory, first step to manipulation of this fungus, so that it synthesizes oligosaccharides that are convertible to complex structures in the simplest possible way. If the first steps of the complex carbohydrate synthesis pathway would occur in vivo in a fungus, such as Trichoderma, completion of the glycosylation pathway could be carried out by in vitro enzymatic oligosaccharide modification on proteins. We believe that large scale, stereocontrolled oligosaccharide synthesis will be possible in the future: much research is in progress to reduce the high expenses associated with these in vitro processing steps (Ichikawa et al., 1992). Finally, another important aspect concerning this research can be mentioned: the fact that a fungus can be manipulated to synthesize well-defined and uniform glycosyl structures on its secreted proteins. For certain proteins, the production of single glycoform may be desired to obtain an uniform therapeutic profile.

Example 15

Transformation of *T. reesei* with GlcNAc Tr I coding sequences and Expression of Modified Glycoprotein from the Trichoderma Host A DNA vector is constructed that contains the coding sequence of human GlcNAc Tr I (Genbank Accession No. M55621; EMBL ID No. HSGLCNAC) as described above, and such that the DNA providing coding sequence for the GlcNAc Tr I enzyme is operably linked to the CBHI promoter and terminator. Such vector is transformed into *T. reesei*, using the technique described in EP 244,234, and positive transformants selected.

One of the positive transformants is futher transformed with a second vector, encoding ovalbumin in a form that was secreted from the Trichoderma host, and transformants were selected that expressed both GlcNAc Tr I and ovalbumin.

Ovalbumin that is secreted into the Trichodenna medium is already processed to a first hybrid form by the intracellular action of GlcNAc Tr I. This ovalbumin is further processed using β 1,4 galactosyltransferase and α 2,6 sialyltransferase as described in Example 11.

Example 16

Transformation of *T. reesei* with GlcNAc Tr I coding sequences and Expression of Modified Glycoprotein from the Trichoderma Host As in Example 15, except that the ovalbumin is processed with non-specific α-mannosidase after treatment with β 1,4 galactosyl transferase, or after treatment with α 2,6 sialyltransferase.

Example 17

Transformation of *T. reesei* with GlcNAc Tr I coding sequences and Expression of Modified Glycoprotein from the Trichoderma Host As in Example 15 or Example 16, except that the gene of interest encodes erythropoietin (EPO), human choriogonadotropin (HCG), follitropin (FSH), thyrotropin (TSH), lutropin (LH) NCAM, tenascin, thrombospondin, fibronectin, hormones, cytokines, interleukin-4, interferon gamma, growth factors, plasma proteins, coagulation factors, soluble receptors, an antibody, granulocyte-macrophage colony stimulating factor (GM-CSF), vascular endothelial growth factor, HIV virus glycoprotein gp120, viral coat proteins, immunoglobulin D, antithrombin IIIβ, plasminogen, von Willebrand factor, fibrinogen, corticosteroid-binding globulin, thyroxine-binding globulin, folate-binding protein, fibrinectin, bone and platelet osteonectin, EGF receptor, insulin and insulin-like growth factor-I receptors, basic fibroblast growth factor receptor, lymphocyte CD2, MHC Class II molecules, glucose transporters, erythrocyte band 3 protein, β-2 adrenergic receptors, transferrin receptor, VIP receptor, membrane class I MHC protein, vasopressin receptor of LLC-PK1 cells, low density lipoprotein receptor, asialoglycoprotein receptor, CD4 protein, thyrotropin receptor, PDGF receptor, jack bean concanavalin A, cobra venom factor, lactotransferrin, spinach chloroplast coupling factor, submaxillary gland mucin, intestinal brush border lactase-phlorizin hydrolase, arctic fish antifreeze glycoprotein, LDL receptor, glucophorin A or β-HCG, a peptide subunit of any of the above, or a functional fragment of any of the above.

Example 18

Modification of Proteins Produced in Yeast

A protein of interest, especially one described in Examples 15 and 17 is produced in a yeast selected from *Pichia spp* (especially *Pichia pastoris*), *Hansenula spp* (especially *Hansenula polymorpha*), *Kluyveromyces lactis*, *Yarrowia lipolytica*, or *S. cerevisiae* and treated as described in Example 12 with an α-1,2 mannosidase prior to sequential treatment with GlcNAc Tr I, β-1,4 galactosyl transferase and α2,6-sialyl transferase.

What is claimed is:

1. A process for producing a hybrid glycoprotein, said process comprising:
(a) reacting a high mannose type glycoprotein that has been produced in filamentous fungi with GlcNAc Tr I in the presence of a UDP-GlcNAc sugar nucleotide;
(b) reacting the glycoprotein product of step (a) with β-1,4 galactosyltransferase in the presence of a UDP-galactose sugar nucleotide; and
(c) reacting the glycoprotein product of step (b) with a sialyltransferase in the presence of a CMP-sialic acid sugar nucleotide; wherein said filamentous fungus is a member of the group consisting of: Aspergillis and Trichoderma.

2. The process of claim 1, wherein said glycoprotein is a protein that is homologous to said fungus.

3. The process of claim 1, wherein said glycoprotein is a protein that is heterologous to said fungus.

4. The process of claim 1, wherein said filamentous fungus is a Trichoderma.

5. The process of claim 4, wherein said filamentous fungus is *Trichoderma reesei*.

6. The process of claim 1, wherein said filamentous fungus expresses recombinant GlcNAc Tr I and step (a) occurs intracellularly in said filamentous fungus.

7. The process of claim 1, wherein said filamentous fungus is *Aspergillus niger*.

8. The process of claim 1, wherein steps (a), (b) and (c) are performed in vitro.

9. The process of claim 8, wherein said glycoprotein is reacted with α-1,2 mannosidase between steps (a) and (b).

10. A process for producing a hybrid glycoprotein, said method comprising:
(a) reacting a high mannose type glycoprotein expressed in yeast or a filamentous fungus with an α-1,2-mannosidase;
(b) reacting the glycoprotein product of step (a) with GlcNAc Tr I in the presence of a UDP-GlcNAc sugar nucleotide;
(c) reacting the glycoprotein product of step (b) with β-1,4 galactosyltransferase in the presence of a UDP-galactose sugar nucleotide; and
(d) reacting the glycoprotein product of step (c) with a sialyltransferase in the presence of a CMP-sialic acid sugar nucleotide; wherein said yeast or said filamentous fungus is selected from the group consisting of: *Aspergillus, Trichoderma, Pichia pastoris, Hansenula polymorpha, Kluyveromyces lactis, Saccharomyces cerevisiae* and *Yarrowia lipolytica*.

11. The process of claim 10, wherein steps (a) and (b) occur intracellularly in said yeast or filamentous fungus, and steps (c) and (d) are performed in vitro.

12. The process of claim 11, wherein said high mannose glycoprotein was produced in a yeast, and steps (a) and (b) occur intracellularly in said yeast.

13. The process of claim 12, wherein said yeast is selected from the group consisting of *Pichia pastoris, Hansenula polymorpha, Kluyveromyces lactis, S. cerevisiae*, and *Yarrowia lipolytica*.

14. The process of claim 13, wherein said yeast is *Pichia pastoris*.

15. The process of claim 13, wherein yeast is *Hansenula polymorpha*.

16. The process of claim 13, wherein said yeast is *S. cerevisiae*.

17. The process of claim 10, wherein said high mannose glycoprotein was produced in Aspergillus, or Trichoderma.

18. The process of claim 11, wherein said high mannose type glycoprotein is expressed in a Trichoderma.

19. The process of claim 18, wherein said Trichoderma is *Trichoderma reesei*.

20. The process of claim 10, wherein step (a) occurs intracellularly in said yeast or filamentous fungus, and steps (b), (c), and (d) are performed in vitro.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:1:

CCAGGATGCT GAAGAAGCAG TCTGCA                                                          26

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: Not Relevant
        ( D ) TOPOLOGY: Not Relevant ( i i ) MOLECULE TYPE: DNA (genomic)

( x i ) SEQUENCE DESCRIPTION: SEQ ID NO:2:

CCAGTCGACA GGTGCTAATT CCAGCTAG                                                     28

( 2 ) INFORMATION FOR SEQ ID NO:3:

( i ) SEQUENCE CHARACTERISTICS:
        ( A ) LENGTH: 41 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:3:

```
    Met Leu Lys Lys Gln Ser Ala Gly Leu Val Leu Trp Gly Ala Ile Leu
    1               5                   10                  15

Phe Val Ala Trp Asn Ala Leu Leu Leu Leu Phe Phe Trp Thr Arg Pro
                    20                  25                  30

Ala Pro Gly Arg Pro Pro Ser Val Ser
                    35                  40
```

( 2 ) INFORMATION FOR SEQ ID NO:4:

( i ) SEQUENCE CHARACTERISTICS:
        ( A ) LENGTH: 255 base pairs
        ( B ) TYPE: nucleic acid
        ( C ) STRANDEDNESS: Not Relevant
        ( D ) TOPOLOGY: Not Relevant ( i i ) MOLECULE TYPE: peptide ( i x ) FEATURE:
        ( A ) NAME/KEY: CDS
        ( B ) LOCATION: 1..255

( x i ) SEQUENCE DESCRIPTION: SEQ ID NO:4:

```
ATG AGA TTT CCT TCA ATT TTT ACT GCA GTT TTA TTC GCA GCA TCC TCC    48
Met Arg Phe Pro Ser Ile Phe Thr Ala Val Leu Phe Ala Ala Ser Ser
1               5                   10                  15
```

-continued

| GCA | TTA | GCT | GCT | CCA | GTC | AAC | ACT | ACA | ACA | GAA | GAT | GAA | ACG | GCA | CAA | 96 |
|---|---|---|---|---|---|---|---|---|---|---|---|---|---|---|---|---|
| Ala | Leu | Ala | Ala | Pro | Val | Asn | Thr | Thr | Thr | Glu | Asp | Glu | Thr | Ala | Gln | |
| | | | 20 | | | | | 25 | | | | | 30 | | | |

| ATT | CCG | GCT | GAA | GCT | GTC | ATC | GGT | TAC | TCA | GAT | TTA | GAA | GGG | GAT | TTC | 144 |
|---|---|---|---|---|---|---|---|---|---|---|---|---|---|---|---|---|
| Ile | Pro | Ala | Glu | Ala | Val | Ile | Gly | Tyr | Ser | Asp | Leu | Glu | Gly | Asp | Phe | |
| | | 35 | | | | | 40 | | | | | 45 | | | | |

| GAT | GTT | GCT | GTT | TTG | CCA | TTT | TCC | AAC | AGC | ACA | AAT | AAC | GGG | TTA | TTG | 192 |
|---|---|---|---|---|---|---|---|---|---|---|---|---|---|---|---|---|
| Asp | Val | Ala | Val | Leu | Pro | Phe | Ser | Asn | Ser | Thr | Asn | Asn | Gly | Leu | Leu | |
| | 50 | | | | | 55 | | | | | | 60 | | | | |

| TTT | ATA | AAT | ACT | ACT | ATT | GCC | AGC | ATT | GCT | GCT | AAA | GAA | GAA | GGG | GTA | 240 |
|---|---|---|---|---|---|---|---|---|---|---|---|---|---|---|---|---|
| Phe | Ile | Asn | Thr | Thr | Ile | Ala | Ser | Ile | Ala | Ala | Lys | Glu | Glu | Gly | Val | |
| 65 | | | | | 70 | | | | | 75 | | | | | 80 | |

| TCT | TTG | GAT | AAA | AGG | | | | | | | | | | | | 255 |
|---|---|---|---|---|---|---|---|---|---|---|---|---|---|---|---|---|
| Ser | Leu | Asp | Lys | Arg | | | | | | | | | | | | |
| | | | | 85 | | | | | | | | | | | | |

( 2 ) INFORMATION FOR SEQ ID NO:5:

( i ) SEQUENCE CHARACTERISTICS:
        ( A ) LENGTH: 85 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| Met | Arg | Phe | Pro | Ser | Ile | Phe | Thr | Ala | Val | Leu | Phe | Ala | Ala | Ser | Ser |
|---|---|---|---|---|---|---|---|---|---|---|---|---|---|---|---|
| 1 | | | | 5 | | | | | 10 | | | | | 15 | |

| Ala | Leu | Ala | Ala | Pro | Val | Asn | Thr | Thr | Thr | Glu | Asp | Glu | Thr | Ala | Gln |
|---|---|---|---|---|---|---|---|---|---|---|---|---|---|---|---|
| | | | 20 | | | | | 25 | | | | | 30 | | |

| Ile | Pro | Ala | Glu | Ala | Val | Ile | Gly | Tyr | Ser | Asp | Leu | Glu | Gly | Asp | Phe |
|---|---|---|---|---|---|---|---|---|---|---|---|---|---|---|---|
| | | 35 | | | | | 40 | | | | | 45 | | | |

| Asp | Val | Ala | Val | Leu | Pro | Phe | Ser | Asn | Ser | Thr | Asn | Asn | Gly | Leu | Leu |
|---|---|---|---|---|---|---|---|---|---|---|---|---|---|---|---|
| | 50 | | | | | 55 | | | | | | 60 | | | |

| Phe | Ile | Asn | Thr | Thr | Ile | Ala | Ser | Ile | Ala | Ala | Lys | Glu | Glu | Gly | Val |
|---|---|---|---|---|---|---|---|---|---|---|---|---|---|---|---|
| 65 | | | | | 70 | | | | | 75 | | | | | 80 |

| Ser | Leu | Asp | Lys | Arg |
|---|---|---|---|---|
| | | | | 85 |